(12) United States Patent
Castro-Gonzalez et al.

(10) Patent No.: US 9,984,277 B2
(45) Date of Patent: May 29, 2018

(54) SYSTEMS, APPARATUS, AND METHODS FOR ANALYZING BLOOD CELL DYNAMICS

(71) Applicant: Massachusetts Institute of Technology, Cambridge, MA (US)

(72) Inventors: Carlos Castro-Gonzalez, Cambridge, MA (US); Ian Butterworth, Cambridge, MA (US); Aurelien Bourquard, Cambridge, MA (US); Alvaro Sanchez-Ferro, Madrid (ES)

(73) Assignee: Massachusetts Institute of Technology, Cambridge, MA (US)

( * ) Notice: Subject to any disclaimer, the term of this patent is extended or adjusted under 35 U.S.C. 154(b) by 238 days.

(21) Appl. No.: 14/951,260

(22) Filed: Nov. 24, 2015

(65) Prior Publication Data

US 2016/0148038 A1 May 26, 2016

Related U.S. Application Data

(60) Provisional application No. 62/137,441, filed on Mar. 24, 2015, provisional application No. 62/083,712, filed on Nov. 24, 2014.

(51) Int. Cl.
*G06K 9/00* (2006.01)
*G06T 1/20* (2006.01)
(Continued)

(52) U.S. Cl.
CPC .......... *G06K 9/00127* (2013.01); *A61B 5/004* (2013.01); *A61B 5/14546* (2013.01);
(Continued)

(58) Field of Classification Search
None
See application file for complete search history.

(56) References Cited

U.S. PATENT DOCUMENTS 4,998,533 A  3/1991 Winkelman
5,598,842 A  2/1997 Ishihara et al.
(Continued)

FOREIGN PATENT DOCUMENTS

KR  10-2013-0028484  3/2013
WO  WO 2001/022741 A2  3/2001

OTHER PUBLICATIONS

Etehad Tavakol, Mahnaz, et al. "Nailfold capillaroscopy in rheumatic diseases: which parameters should be evaluated?." BioMed research international 2015 (2015).*
(Continued)

*Primary Examiner* — Nirav G Patel
(74) *Attorney, Agent, or Firm* — Cooley LLP

(57) ABSTRACT

Systems, apparatus, and methods for non-invasively detecting a white blood cell (WBC) event from in vivo capillary data may include obtaining a plurality of images, followed by specifying two-dimensional (2D) coordinates corresponding to internal contour and external contour of a capillary visible in the images. The two sets of 2D coordinates may be resampled to generate two sets of resampled coordinates, between which intermediate curves, including a middle curve, are generated. Curvilinear distances may be defined based on the middle curve. Intensity values, each of which corresponds to one of the images, one of the intermediate curves, and one of the curvilinear distances, may be extracted and transformed to the Radon domain. A plurality of maxima locations in the Radon domain corresponding to a flow trajectory inside the capillary may be identified. Detection of a visual gap in the flow trajectory inside the capillary indicates a WBC event.

33 Claims, 30 Drawing Sheets

(51) Int. Cl.
*G06T 7/00* (2017.01)
*G06T 5/50* (2006.01)
*A61B 5/00* (2006.01)
*G06K 9/52* (2006.01)
*G06K 9/62* (2006.01)
*A61B 5/145* (2006.01)
*G06T 7/33* (2017.01)
*G06T 7/12* (2017.01)
*G06T 7/136* (2017.01)
*G01N 15/14* (2006.01)

(52) U.S. Cl.
CPC .......... *A61B 5/6826* (2013.01); *A61B 5/6898* (2013.01); *G06K 9/0014* (2013.01); *G06K 9/522* (2013.01); *G06K 9/6215* (2013.01); *G06T 1/20* (2013.01); *G06T 5/50* (2013.01); *G06T 7/0012* (2013.01); *G06T 7/12* (2017.01); *G06T 7/136* (2017.01); *G06T 7/33* (2017.01); *A61B 5/7425* (2013.01); *A61B 2560/0462* (2013.01); *A61B 2576/02* (2013.01); *G01N 15/1475* (2013.01); *G06T 2207/10016* (2013.01); *G06T 2207/10024* (2013.01); *G06T 2207/10056* (2013.01); *G06T 2207/10152* (2013.01); *G06T 2207/20076* (2013.01); *G06T 2207/20096* (2013.01); *G06T 2207/30024* (2013.01); *G06T 2207/30101* (2013.01); *G06T 2207/30104* (2013.01); *G06T 2207/30242* (2013.01)

(56) References Cited

U.S. PATENT DOCUMENTS

| | | | |
|---|---|---|---|
| 5,934,278 | A | 8/1999 | Ishihara et al. |
| 5,983,120 | A | 11/1999 | Groner et al. |
| 2005/0209514 | A1 | 9/2005 | Oshima et al. |
| 2006/0060770 | A1 | 3/2006 | Page et al. |
| 2006/0161063 | A1 | 7/2006 | Shau |
| 2008/0079723 | A1* | 4/2008 | Hanson ................ G06K 9/0063 345/427 |
| 2009/0093970 | A1 | 4/2009 | Lewy et al. |
| 2013/0011055 | A1 | 1/2013 | You et al. |
| 2013/0235949 | A1 | 9/2013 | Jeckeln |
| 2014/0038206 | A1 | 2/2014 | Holmes et al. |
| 2014/0085482 | A1 | 3/2014 | Teich et al. |
| 2014/0092377 | A1 | 4/2014 | Liu et al. |
| 2014/0160481 | A1 | 6/2014 | Ahner et al. |
| 2014/0232869 | A1 | 8/2014 | May et al. |

OTHER PUBLICATIONS

Allen et al., "Computer based system for acquisition and analysis of nailfold capillary images," *Medical Image Understanding & Analysis*, (2003): 1-4.

Anderson et al., "Computerized nailfold video capillaroscopy—a new tool for assessment of raynaud's phenomenon," *J. Rheumatology* 32.5 (2005): 841-848.

Brown et al., "Rigidity of Circulating Lymphocytes is Primarily Conferred by Vimentin Intermediate Filaments", *The Journal of Immunology*, 166.11 (2001): 6640-6646.

Delgado-Gonzalo et al., "Spline-based framework for interactive segmentation in biomedical imaging," *IRBM* 34.3 (2013): 235-243.

Eden et al., "An automated method for analysis of flow characteristics of circulating particles from in vivo video microscopy," *IEEE Transactions on Medical Imaging* 24.8 (2005): 1011-1024.

Golan et al., "Noninvasive imaging of flowing blood cells using label-free spectrally encoded flow cytometry," *Biomed Opt Express* 3.6 (2012): 1455-1464.

Hofstee et al., "A multicentre study on the reliability of qualitative and quantitative nail-fold videocapillaroscopy assessment," *Rheumatology* (2011): ker403.

Hollis et al., "Comparison of venous and capillary differential leukocyte counts using a standard hematology analyzer and a novel microfluidic impedance cytometer," *PloS One* 7.9 (2012): e43702.

Huang et al., "'A SR-based radon transform to extract weak lines from noise images," in Proceedings Int Conf on Image Processing, Barcelona, Spain 1 (2003): 849-852.

Kaur et al., "Nailfold Capillaryscopy Techniques—A Review," *IRACST—IJCSITS* 2.2 (2012): 326-331.

MacLennan et al., "Finger-prick blood samples can be used interchangeably with venous samples for CD4 cell counting indicating their potential for use in CD4 rapid tests," *AIDS* 21.12 (2007): 1643-1645.

Mugii, et a., "Reduced red blood cell velocity in nail-fold capillaries as a sensitive and specific indicator of microcirculation injury in systemic sclerosis," *Rheumatology* 48.6 (2009): 696-703.

Rao et al., "Evaluation of a new point of care automated complete blood count (CBC) analyzer in various clinical settings," *Clinica Chimica Acta* 389.1-2 (2008): 120-125.

Riva et al., "Blue field entoptic phenomenon and blood velocity in the retinal capillaries," *JOSA* 70.10 (1980): 1234-1238.

Russcher et al., "Evaluation of the HemoCue WBC DIFF system for point-of-care counting of total and differential white cells in pediatric samples," *Ned Tijdschr Klin Chem Labgeneesk* 38.3 (2013): 140-141.

Uji et al., "The source of moving particles in parafoveal capillaries detected by adaptive optics scanning laser ophthalmoscopy," *Investigative Ophthalmology & Visual Science* 53.1 (2012): 171-178.

Winkelman et al., "Noninvasive Blood Cell Measurements by Imaging of the Microcirculation," *Am J Clin Pathol* 113 (2000): 479-483.

Yap et al., "Mechanical deformation of neutrophils into narrow channels induces pseudopod projection and changes in biomechanical properties", *Journal of Applied Physiology* 98.5 (2005): 1930-1939.

International Search Report and Written Opinion issued for PCT/US15/62487, dated Feb. 5, 2016.

* cited by examiner

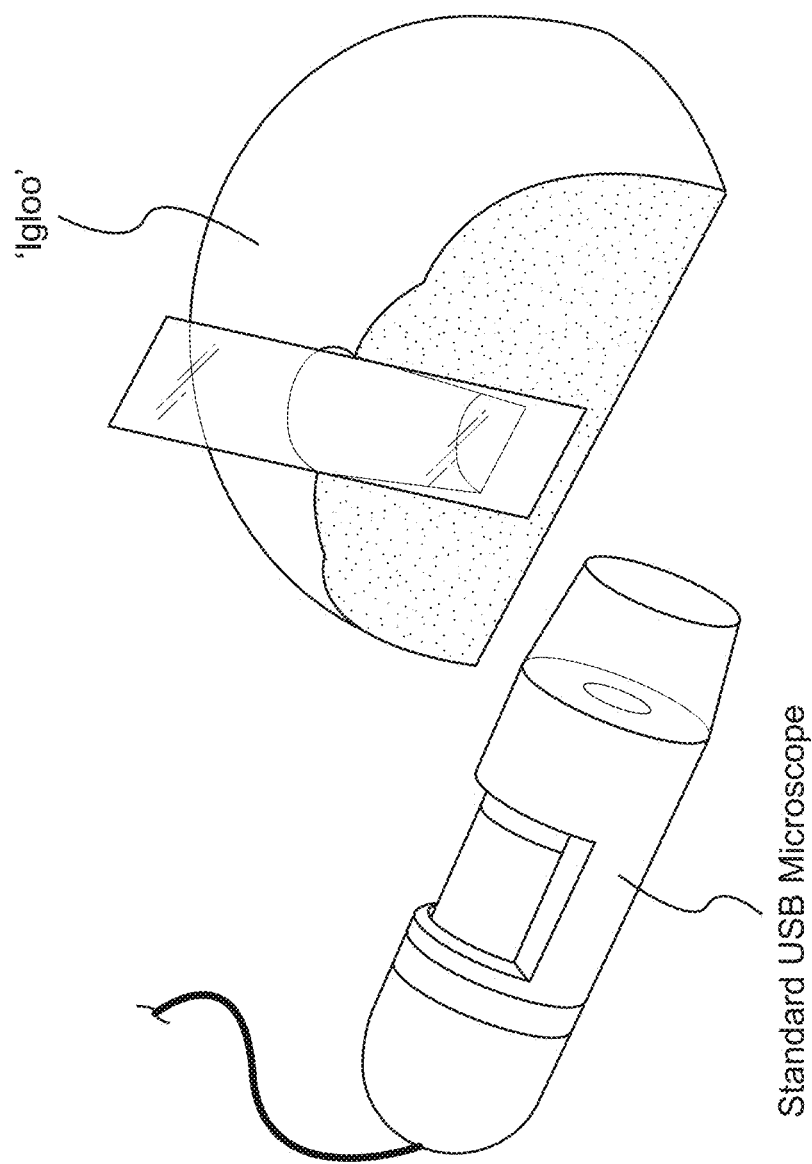

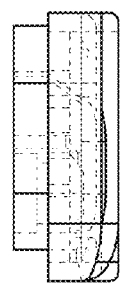
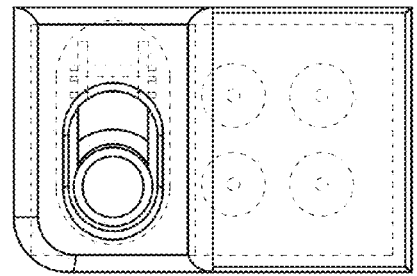
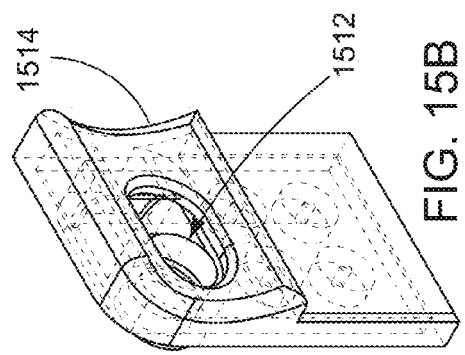
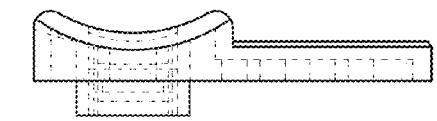
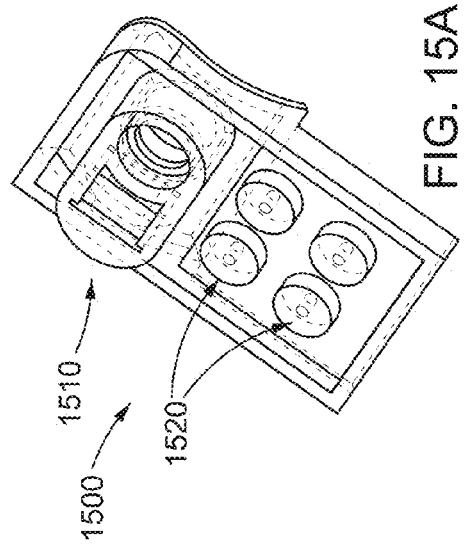
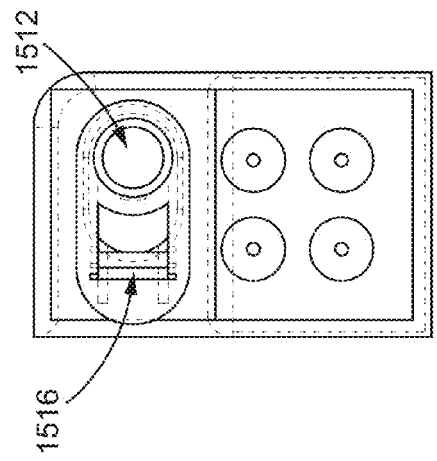
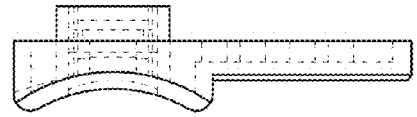

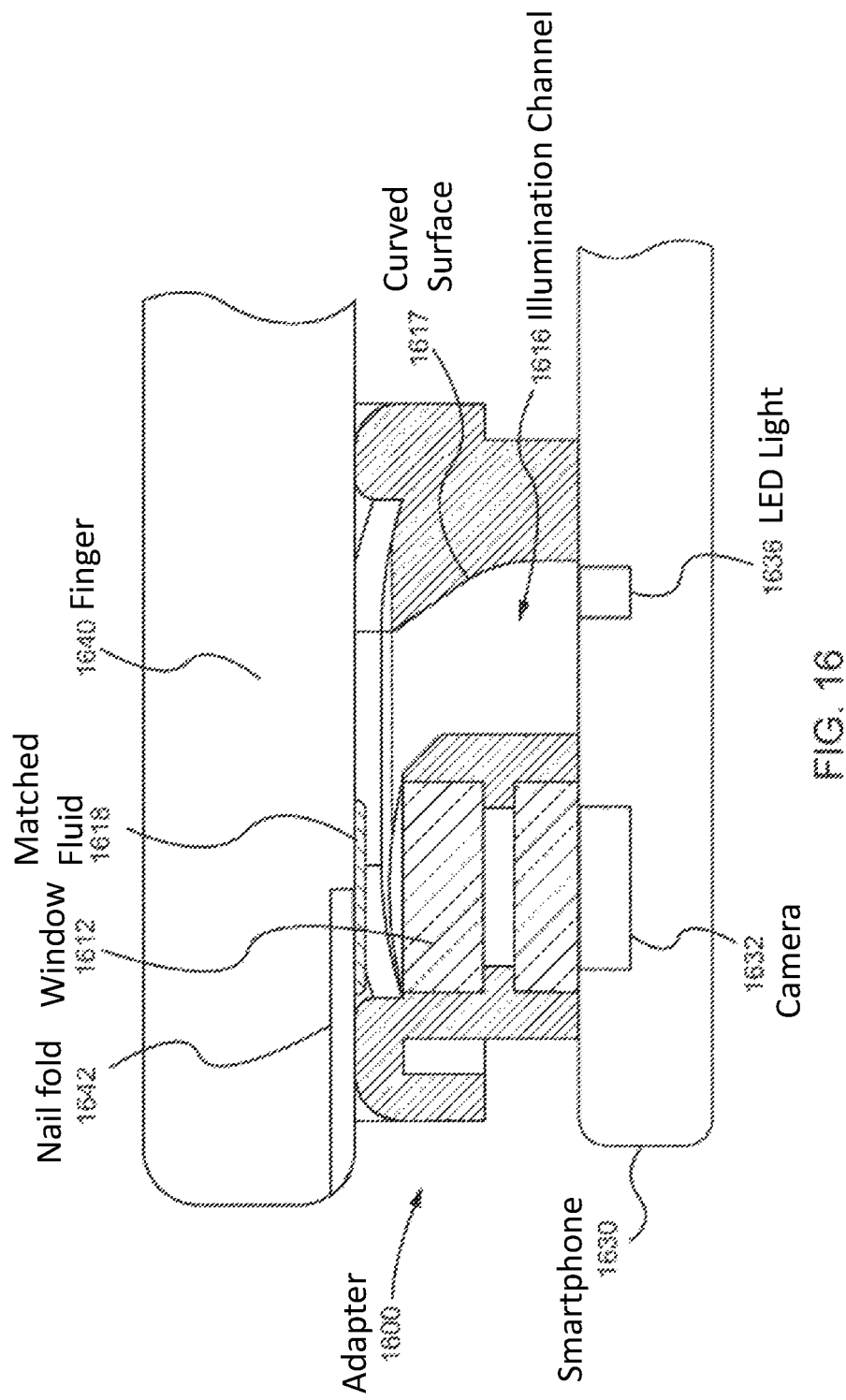

SYSTEMS, APPARATUS, AND METHODS FOR ANALYZING BLOOD CELL DYNAMICS

CROSS-REFERENCE TO RELATED APPLICATIONS

This application claims a priority benefit of U.S. Provisional Patent Application No. 62/083,712, filed on Nov. 24, 2014, and entitled "IMAGE PROCESSING ALGORITHM TO EXTRACT WHITE BLOOD CELL COUNTS FROM NON-INVASIVE, IN-VIVO, TIME-LAPSE IMAGES OF NAILFOLD CAPILLARIES," and U.S. Provisional Patent Application No. 62/137,441, filed on Mar. 24, 2015, and entitled "IMAGE PROCESSING ALGORITHM TO EXTRACT WHITE BLOOD CELL COUNTS FROM NON-INVASIVE, IN-VIVO, TIME-LAPSE IMAGES OF NAILFOLD CAPILLARIES," which applications are incorporated herein by reference in their entirety.

TECHNICAL FIELD

The present disclosure relates generally to systems, apparatus, and methods for analyzing blood cell dynamics. More specifically, the present disclosure relates to systems, apparatus, and methods for extracting white blood cell information from non-invasive, in vivo, and/or time-lapse images.

BACKGROUND

White blood cells (WBCs, also referred to as leukocytes or leucocytes) are cells of the immune system that are involved in protecting the body against both infectious disease and foreign invaders. WBCs can exist not only in the blood, but also in the lymphatic system and tissues. Some conditions can trigger a response in the immune system and cause an increase in the number of WBCs (also referred to as WBC count). Other conditions can affect the production of WBCs by the bone marrow or the survival of existing WBCs in the circulation system. Either way, these conditions can cause a change (either an increase or a decrease) of the number of circulating WBCs. Therefore, WBC counts can be a relevant physiological parameter for the diagnosis, monitoring, and treatment of various conditions including, but not limited to, bacterial and viral infections (e.g., pneumonia or meningitis), bone marrow functionality associated with chemotherapy toxicity, and haematologic proliferative processes such as leukaemia.

In current clinical practice, most of the tests to derive WBC count are performed with large-scale equipment in central clinical laboratories. Generally, these ex vivo tests are still invasive because blood samples (usually a full vial of blood is needed for each test) are collected from a patient. These blood samples are then transported, queued, and analyzed in laboratory tests, thereby taking several days to receive any results. This procedure can be burdensome for patients who need regular WBC counts or for patients with emergent conditions as well as their car. In addition, due to the ex vivo nature of conventional blood tests, there can be a certain bias of some parameters owing to the inherent differences between the measurements and the true physiological properties.

SUMMARY

Systems, apparatus, and methods for analyzing blood cell dynamics are disclosed. In one example, a method for detecting a white blood cell (WBC) event from in vivo capillary data associated with a subject includes non-invasively obtaining the capillary data including a plurality of images captured over a first time period. The method also includes specifying a first set of two-dimensional (2D) coordinates associated with the plurality of images. The first set of 2D coordinates corresponds to a plurality of internal contour points of a capillary visible in the plurality of images. The method also includes specifying a second set of 2D coordinates associated with the plurality of images. The second set of 2D coordinates corresponds to a plurality of external contour points of the capillary. The method then interpolates the first set of 2D coordinates to generate a first set of resampled coordinates and interpolates the second set of 2D coordinates to generate a second set of resampled coordinates. The method further includes generating a plurality of intermediate curves based on the first set of resampled coordinates and the second set of resampled coordinates. The plurality of intermediate curves includes a middle curve, based on which a plurality of curvilinear distances is defined. The method further includes extracting a plurality of intensity values from the plurality of images. Each extracted intensity value corresponds to one of the plurality of images, one of the plurality of intermediate curves, and one of the plurality of curvilinear distances. The plurality of extracted intensity values are then transformed to a Radon domain, in which a plurality of maxima locations corresponding to a flow trajectory inside the capillary are identified. The method further includes detecting at least one visual gap in the flow trajectory inside the capillary, the at least one visual gap indicating the WBC event.

In another example, an apparatus for detecting a white blood cell (WBC) event from in vivo capillary data associated with a subject includes an imager to take the capillary data including a plurality of images captured over a first time period, a memory to store processor executable instructions, and a processor coupled to the imager and the memory. Upon execution of the processor executable instruction by the processor, the processor receives the plurality of images captured by the imager. The processor also receives a first set of two-dimensional (2D) coordinates associated with the plurality of images. The first set of 2D coordinates corresponds to a plurality of internal contour points of a capillary visible in the plurality of images. The processor also receives a second set of 2D coordinates associated with the plurality of images. The second set of 2D coordinates corresponds to a plurality of external contour points of the capillary. The process then interpolates the first set of 2D coordinates to generate a first set of resampled coordinates and interpolates the second set of 2D coordinates to generate a second set of resampled coordinates. The processor also generates a plurality of intermediate curves based on the first set of resampled coordinates and the second set of resampled coordinates. The plurality of intermediate curves includes a middle curve, based on which the processor defines a plurality of curvilinear distances. The processor then extracts a plurality of intensity values from the plurality of images. Each extracted intensity value corresponds to one of the plurality of images, one of the plurality of intermediate curves, and one of the plurality of curvilinear distances. The processor further transforms the plurality of extracted intensity values to a Radon domain, in which a plurality of maxima locations corresponding to a flow trajectory inside the capillary is identified. The processor also detects at least one visual gap in the flow trajectory inside the capillary, the at least one visual gap indicating the WBC event.

In yet another example, a computer-readable medium is encoded with instructions that, when executed on at least one processing unit, perform a method for detecting a white blood cell (WBC) event from in vivo capillary data associated with a subject. The method includes non-invasively obtaining the capillary data including a plurality of images captured over a first time period. The method also includes specifying a first set of two-dimensional (2D) coordinates associated with the plurality of images. The first set of 2D coordinates corresponds to a plurality of internal contour points of a capillary visible in the plurality of images. The method also includes specifying a second set of 2D coordinates associated with the plurality of images. The second set of 2D coordinates corresponds to a plurality of external contour points of the capillary. The method then interpolates the first set of 2D coordinates to generate a first set of resampled coordinates and interpolates the second set of 2D coordinates to generate a second set of resampled coordinates. The method further includes generating a plurality of intermediate curves based on the first set of resampled coordinates and the second set of resampled coordinates. The plurality of intermediate curves includes a middle curve, based on which a plurality of curvilinear distances is defined. The method further includes extracting a plurality of intensity values from the plurality of images. Each extracted intensity value corresponds to one of the plurality of images, one of the plurality of intermediate curves, and one of the plurality of curvilinear distances. The plurality of extracted intensity values are then transformed to a Radon domain, in which a plurality of maxima locations corresponding to a flow trajectory inside the capillary are identified. The method further includes detecting at least one visual gap in the flow trajectory inside the capillary, the at least one visual gap indicating the WBC event.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 14A-14D are images of systems and apparatus for analyzing blood cell dynamics analysis in accordance with some embodiments.

FIGS. 15A-15J are views of an adapter for capturing images of a nailfold with a smartphone camera for blood cell dynamics analysis in accordance with some embodiments.

FIG. 16 is a schematic of a system including a smartphone and an adapter for capturing images of a nailfold for blood cell dynamics analysis in accordance with some embodiments.

DETAILED DESCRIPTION

In view of the problems with conventional blood tests, it can be beneficial to develop non-invasive and in vivo techniques to derive WBC counts. These non-invasive and in vivo techniques allow more frequent monitoring, less visits to clinics, and more ready access to testing in areas lacking proper laboratory facilities or reagent supplies.

Non-invasive WBC count techniques that exploit the optical properties of WBCs may be used to observe the WBCs as gaps in retinal capillaries or moving particles in oral mucosa capillaries. However, specialized and/or non-portable devices (e.g., adaptive optics and confocal microscopy) may be required to derive WBC counts. Optical devices referred to as capillaroscopes may be used to acquire optical images of the morphology of nailfold capillaries and diagnose rheumatological diseases; however, the acquired images require time-consuming analysis by trained human reviewers.

Overview of Non Invasive and In Vivo Analysis of Blood Cell Dynamics

Figure 1:
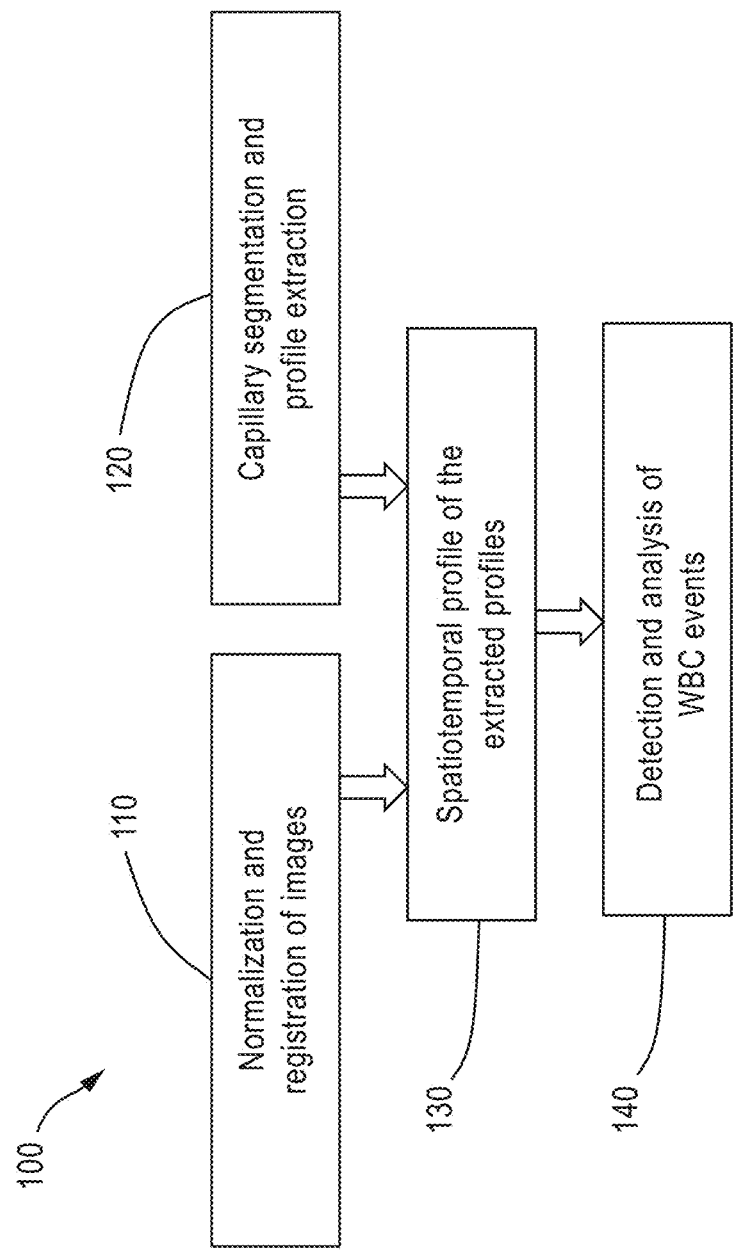
FIG. 1 is a flow chart illustrating methods of analyzing blood cell dynamics in accordance with some embodiments.

FIG. 1 is a flow chart illustrating non-invasive and in vivo methods of analyzing blood cell dynamics according to some embodiments, including but not limited to, detecting a number of WBCs passing through a given capillary over a time period, the speed of one or more of the WBCs flowing through the capillary, and the total number of WBC events per μL.

More specifically, method 100 illustrated in FIG. 1 includes step 110, at which source image(s) of a subject that contains capillaries are normalized and/or registered. Normalization (also referred to as contrast stretching, histogram stretching, or dynamic arrange expansion) of source images may change the range of pixel intensity values so as to, for example, increase the contrast of images. Registration of source images may align the source images such that same pixel locations on different images correspond to same physical locations on the subject. In some embodiments, the source images are taken within a finite time span, during which the camera, the subject, or both, may be moving. Image registration may address such movements. In image registration, one of the images (e.g., the first image in the sequence, the last image in the sequence, or the image that might have the desired field of view) may be used as a reference image, and the other images in the sequence may be compared to the reference image to make corrections. Corrections may be made to maximize certain image similarity measures that quantify the similarity between the reference image and the other images. Examples of image similarity measures include, for example, cross-correlation, mutual information, sum of squared intensity differences, and ratio image uniformity.

At step 120 of method 100, capillary segmentation and/or profile extraction are performed. Capillary segmentation may be used to identify the segments of capillaries in either the original or the registered images (e.g., by identifying the boundaries of the capillary segments). Profile extraction may be used to extract pixel information within the capillary segments for further analysis. Since WBC information is normally contained only in capillaries, it may be helpful to extract pixel information inside the capillary segments and set aside information in other areas in the images. The pixel information to be extracted may include the locations and values (also referred to as intensities) of the pixels inside the capillary segments. The locations of the pixels in each image may be represented in 2D Cartesian coordinates, and the capillaries may be curved. Therefore, it may be helpful to transform the image from the 2D Cartesian coordinate system into a different coordinate system, in which the same points in the same capillary but on different images in the sequence of images have the same coordinates. One example of such a coordinate system is the curvilinear coordinate system, which uses one point in the curved capillary as the origin point and any other point has a one-dimensional (1D) coordinate that is the distance between that point and the origin point.

At step 130 of method 100, profiles extracted from the sequence of images are compiled into a single image (also referred to as spatiotemporal profile) so as to analyze WBC events. Profiles extracted from each image may include information about spatial distribution (i.e., locations) of WBC events or other events of interest. Profiles extracted from different images, taken at different time points, in the sequence of images may include information about WBC events at different time points. Therefore, the spatiotemporal profile, compiled from all of these extracted profiles from the entire sequence of images, may provide rich information relating to both spatial distribution and temporal evolution of WBC events. For example, traces of a particular WBC may be visualized from the spatiotemporal profile. The velocity of a particular WBC flowing in a capillary also may be derived by, for example, taking into account the time lapse between two or more images in the sequence of images.

At step 140 of method 100, the spatiotemporal profile is processed to detect and/or analyze WBC events. In some embodiments, the processing is manual. A user may inspect the spatiotemporal profile and identify a WBC event by, for example, detecting a visual gap (e.g., pixels having higher or lower pixel values compared to surrounding pixels) in the spatiotemporal profile. The user also may derive the motion traces and flow speed from the spatiotemporal profile. In other embodiments, the processing is automatic or semi-automatic. For example, the spatiotemporal profile may be, for example, transformed to the Radon domain. WBC events then may be detected based on local maxima in the Radon domain. Based on the detected WBC events, additional analysis, such as WBC counts and WBC flow speed, may be derived. Furthermore, WBC counts, flow speed, etc., may be used for subsequent diagnosis, monitoring, and/or treatment of diseases or conditions.

According to some embodiments, systems, apparatus, and methods for analysis of blood cell dynamics are based on in vivo images of capillaries without blood drawing or other invasions into a subject's body and also without removing WBCs from their natural environment in the subject's body. In addition, these systems, apparatus, and methods may be used for real-time or substantially real-time results. For example, the processing of the images (from source images to the detection of WBC events and calculation of the WBC counts) may be performed while new images are being taken. WBC events may be monitored to test the response of a subject's body to a medical treatment, thereby providing feedback regarding the efficiency of the treatment. Furthermore, systems, apparatus, and methods here can identify WBC events from relatively low-resolution, low-frame-rate, and noisy source images. For examples, the source images can be frames of a video clip taken by off-the-shelf cameras, cellphone, or other image taking devices.

Methods of Non Invasive and In Vivo Analysis of Blood Cell Dynamics

Figure 2:
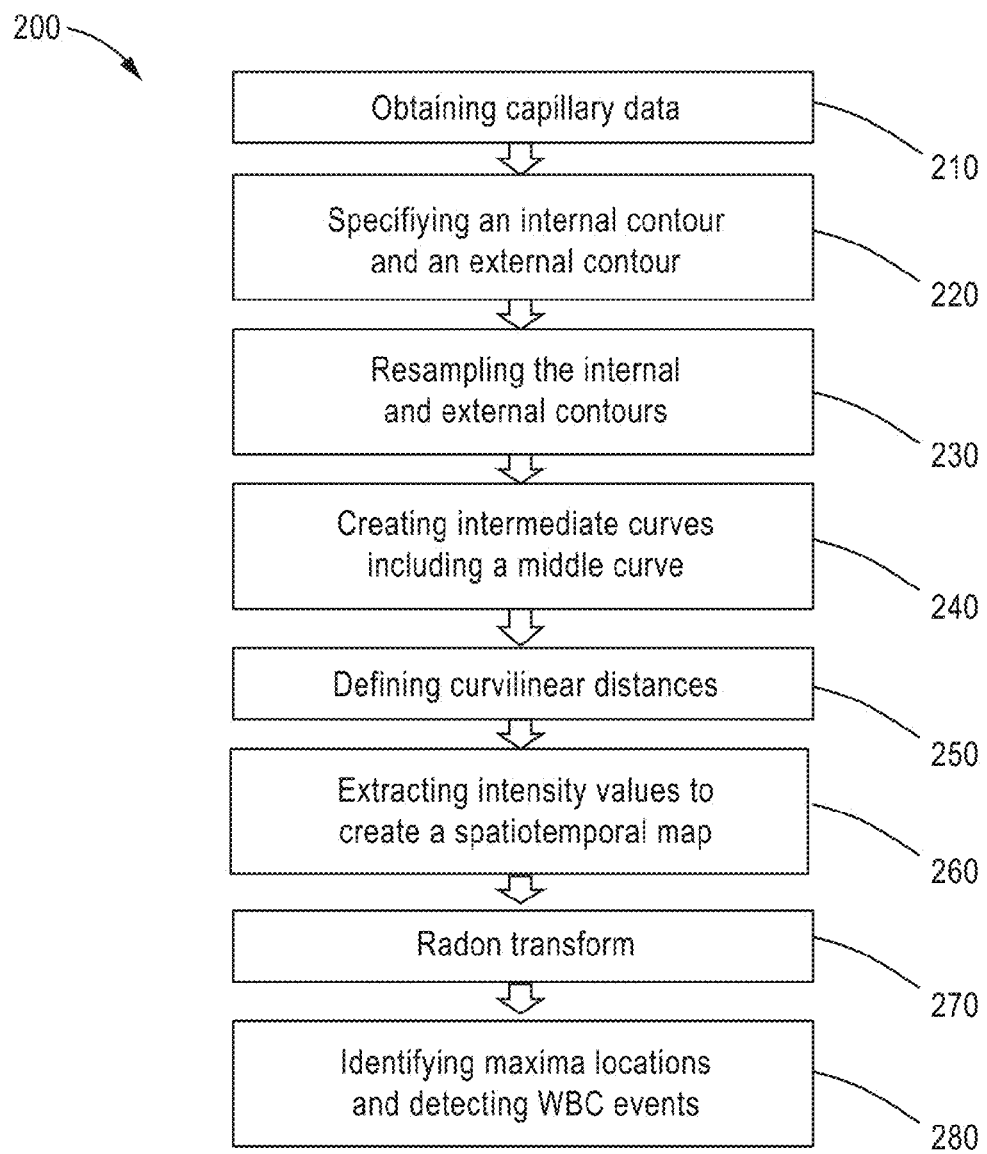
FIG. 2 is a flow chart illustrating methods of analyzing blood cell dynamics using spatiotemporal profiles and Radon transform in accordance with some embodiments.

FIG. 2 is a flow chart illustrating methods of analyzing blood cell dynamics using Radon transforms of spatiotemporal profiles of capillary images according to some embodiments. Method 200 may be used to detect a WBC event from in vivo capillary data associated with a subject. At step 210 of method 200, capillary data is non-invasively obtained. The capillary data may include a plurality of images of one or more capillary segments captured over a first time period.

At step 220 of method 200, the contours of the one or more capillary segments in the images are specified. In particular, for each image in the plurality of images, a first set of two-dimensional (2D) coordinates may be specified to correspond to internal contour points of a capillary segment visible in the images. Step 220 also may include specifying a second set of 2D coordinates corresponding to external contour points of the capillary segment. These sets of 2D coordinates in each image may define the boundaries of the capillary segment in the image.

At step 230 of method 200, each of the first set of 2D coordinates and the second set of 2D coordinates are interpolated so as to generate a first set of resampled coordinates and a second set of resampled coordinates, respectively. The interpolation may fill potential gaps between adjacent contour points specified at step 220 and therefore define smoother boundaries of the one or more capillary segments.

At step 240 of method 200, a plurality of intermediate curves are generated based on the first set of resampled coordinates and the second set of resampled coordinates. These intermediate curves may be within the capillary segment defined by the internal contours points and the external contour points. The plurality of intermediate curves may include a middle curve, which may be used to define a plurality of curvilinear distances as in step 250 of method 200.

In step 260 of method 200, a plurality of intensity values are extracted from the plurality of images. Each extracted intensity value corresponds to one of the plurality of images, one of the plurality of intermediate curves, and one of the plurality of curvilinear distances. That is, each extracted intensity value may be indexed by a vector including three values representing (1) a particular image, (2) a particular intermediate curve, and (3) a particular curvilinear distance.

At step 270 of method 200, the extracted intensity values are transformed to the Radon domain. In step 280 of method 200, a plurality of maxima locations in the Radon domain correspond to a flow trajectory inside the capillary such that a visual gap in the flow trajectory inside the capillary indicates a WBC event.

Capillary Data Collection

According to some embodiments, capillary data (e.g., source images) for the analysis of blood cell dynamics may be obtained from various subjects including, but not limited to, humans and other mammals. In some embodiments, capillary data is collected or captured from one or more locations on or in the body of the subject. For example, capillary data may be collected and/or captured from nailfold capillaries, retinal capillaries, and/or oral mucosa capillaries.

Source images may be captured using various methods. For example, source images may include a sequence of images extracted from a video clip. Each image in the sequence of the images may be captured at a different time point such that the analysis of blood cell dynamics may include, for example, the flow speed of WBCs.

In some embodiments, a location on or in the body of the subject is illuminated by pulsed light sources, and source images are captured by a camera synchronized with the pulsed light sources. For example, a location may be illuminated by pulsed lasers of a particular wavelength (e.g., blue light at about 430 nm), at which WBCs (or other objects of interest) have good reflectivity, so as to improve the contrast of the resulting images.

In some embodiments, the source images include one or more color images such that each pixel in the source images include three values corresponding to, for example, the values of the red, green, and blue components, respectively. In some embodiments, the source images include one or more gray-scale images such that each pixel in the source images has a bit depth of, for example, 2, 4, 6, 7, 8, or 10, corresponding to a gray level of 4, 16, 64, 128, 256, and 1024, respectively.

In some embodiments, the capillary data (e.g., obtained at step 210 in FIG. 2) includes a video acquired in 24-bit RGB format from a given subject. In general, video data may be viewed as a three-dimensional stack I of a sequence of image frames represented as $N_h \times N_v \times N_f$, where $N_h$ and $N_v$ are the horizontal and vertical sizes (also referred to as pixel numbers) of each image frame, respectively, and $N_f$ is the total number of frames in the video data. Each pixel in this video data may be represented as I[k, l], which corresponds to an RGB vector (R[k; 1], G[k; 1], B[k; 1]). The indices $k=(k_1, k_2)$ designate the location of a pixel within a certain frame, and l refers to the index of the frame in the plurality of frames included in the video data. R[k; 1], G[k; 1], and B[k; 1] corresponds to the value of red, green, and blue component, respectively, of the pixel I[k, l]. For example, I[(15, 20), 5] points to a pixel located at the fifteenth row and the twentieth column in the fifth frame of the video data.

Figure 3:
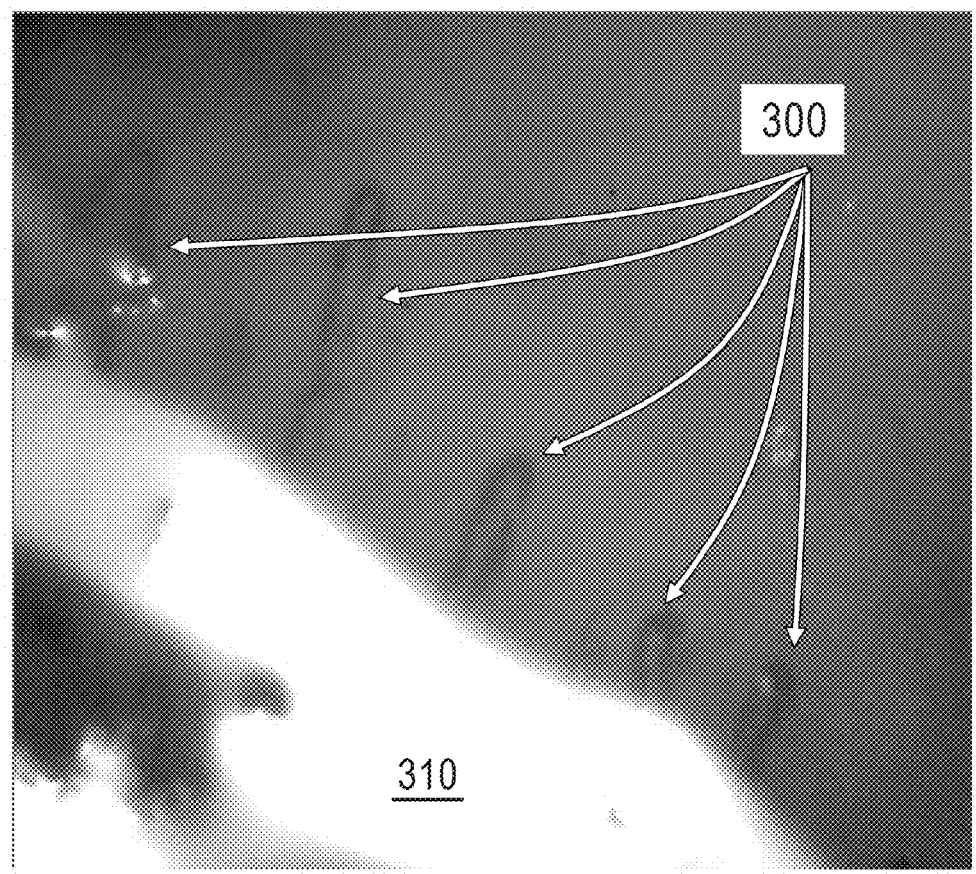
FIG. 3 is an example image of a nailfold that can be used in the methods illustrated in FIGS. 1-2 in accordance with some embodiments.

FIG. 3 is an example image of a human nailfold that may be used in the methods described above for the analysis of blood cell dynamics in one or more of the nailfold capillaries. The image is a frame taken from a nailfold capillaroscopy video, which has a frame rate of r frames per second and a camera pixel size of $S_p$ μm. In FIG. 3, the relatively darker U-shaped profiles of capillaries 300 are readily identifiable in the image, despite the presence of white saturated areas 310 associated with non-ideal acquisition conditions.

Capillary Data Preprocessing

Some pre-processing steps of the images in the capillary data may be performed to facilitate subsequent processing and analysis. These pre-processing steps may include image normalization and/or image registration.

In some embodiments, the capillary data includes one or more grayscale images. Normalization may be used to compress and/or stretch the gray level to a desired range. In some embodiments, the capillary data includes one or more color images. Normalization may be used to convert a color image into a grayscale image before compressing and/or stretching the gray level. The conversion from color images to grayscale images may be achieved via various methods. In one example, the resulting gray level of a color pixel is a sum of the red, green, and blue values in the pixel. In another example, the resulting gray level is the difference between the value of the red component and green component (R-G) so as to emphasize the capillary structures. More sophisticated methods may be employed to calculate the gray level so as to emphasize specific objects of interest (e.g., a WBC or a red blood cell). For example, particular weighted averages of red, green, and blue components may be calculated, or in other types of channel conversion that are non-linear (e.g., RGB to HSV (Hue, Saturation, Value) conversion).

In some embodiments, image registration includes one or more intensity-based methods, which compare intensity patterns in images via correlation metrics. Intensity-based methods can register entire images or sub-images. If sub-images are registered, centers of corresponding sub-images may be treated as corresponding feature points.

In some embodiments, image registration includes one or more feature-based methods, which find correspondence between image features such as points, lines, and contours. Feature-based methods can establish a correspondence between one or more distinct points in an image. Knowing the correspondence between these distinct points in images, a geometrical transformation may be determined to map the target image to other images, thereby establishing point-by-point correspondence between a reference image and other images.

In some embodiments, the capillary data includes a 24-bit RGB format video, including frames like the image in FIG. 3. In these embodiments, stack I may be converted into a single-channel version $I_n$ that can be suitably exploited for further profile segmentation and analysis. The scalar-valued stack $I_n[k; l]$ may be obtained by first averaging the RGB channels of I for each pixel point ("point-wise") and then normalizing the resulting intensities. The normalization may be performed such that the mean and standard deviation of the intensity values of $I_n$ over every given frame l is 0 and 1, respectively. The frames constituting $I_n$ may be registered to, for example, compensate for camera movements. The frame registration may be achieved by applying respective corrective shifts to each frame l>1 of $I_n$, that is, using the first image (l=1) as reference.

More specifically and first, a point-wise operation may be performed to obtain temporary stack $$I'[k;l]=R[k;l]-G[k;l], \quad (1)$$

for all k and l, i.e., $k_1=1, 2, \ldots, N_h$; $k_2=1, 2, \ldots, N_v$; and $k_3=1, 2, \ldots, N_f$. This operation emphasizes capillary-like structures while discarding surrounding artefacts.

Second, binary-thresholded stack $I_t'$ may be obtained using a threshold value $\tau_c$ that is specified for every separate frame of the sequence, the value of which may be determined either experimentally, using a priori information existing in the images (e.g., total brightness, contrast, gray-scale variance, skewness, etc.), or through feature learning from a training dataset. In this step, the pixel value at a location [k; l] in the temporary stack I'[k; l] is set to zero if I'[k; l] is smaller than $\tau_c$ and is set to one if I'[k; l] is equal to or greater than $\tau_c$, that is:

$$I_t[k;l]=0 \text{ if } I'[k;l]<\tau_c \quad (2)$$

and $$I_t[k;l]=1 \text{ if } I'[k;l]>\tau_c \quad (3)$$

Third, a 2D registered stack $I_r$ is calculated such that the applied corrective shifts can maximize the correlation (i.e., the normalized scalar product) between $I_t'[k; l]$ and $I_1'[k; l]$, for l>1.

Capillary Profile Segmentation

Step 220 of method 200 in FIG. 2 is performed to achieve capillary profile segmentation, i.e., identify segments of capillaries in the images, in accordance with some embodiments. In some embodiments, segmentation is performed on the source images (with or without pre-processing). In some embodiments, segmentation is performed on normalized and/or registered images. In some embodiments, segmentation is performed on source images after some other processing, such as noise filtering and/or contrast improvements intended to emphasize capillary structures.

In some embodiments, capillary segmentation is manual. A user may draw lines along the boundaries of the capillaries visible in the images. For example, step 220 may be performed by a user. The user may mark some internal contour points and external contour points on an image, after which a computer may retrieve the 2D coordinates of these marked internal and external contour points for further processing (e.g., resamples at step 230).

In some embodiments, capillary segmentation is automated or semi-automated using methods such as thresholding and/or edge detection. Artificial intelligence methods may be used to train a computer-based pattern recognition model. In one example, a pattern recognition model may be based on historical images of capillaries such that the pattern recognition model can recognize similar capillary structures when a new image is provided. In another example, a pattern recognition model may be based on one or more capillary structures in one portion of an image such that the pattern recognition model can recognize similar capillary structures in other portions of the image.

In some embodiments, capillary segmentation may involve a hybrid approach, in which a user makes some initial and rough indications of the boundaries of capillaries and a computer-based program refines the initial indications using interpolation (e.g., linear interpolation, polynomial interpolation, or spline interpolation), curve fitting (e.g., using linear or nonlinear regression), and/or extrapolation (e.g., using linear extrapolation, polynomial extrapolation, conic extrapolation, or French extrapolation).

In some embodiments, segmentation of each capillary is semi-automated with minimal user-defined 2D coordinates. For example, a user may define two sets of 2D coordinates, $P_{int}[j]$ and $P_{ext}[j]$, with j=1, 2, . . . , $N_p$, that follow the internal and external capillary boundaries as defined on the first frame of the stack I. Here, j is the index of the jth point on the contour, and $N_p$ is the total number of points specified by the user in each contour (internal or external). The total number of specified point $N_p$ can be dependent on several factors including, but not limited to, the complexity of the capillary boundaries and the length of the capillaries. Fewer points can be specified for straight capillaries or straight portions of capillaries, compared to capillaries with sharp turns. In some embodiments, the number of specified points $N_p$ may range from about 3 points to about 20 points. In some embodiments, the number of specified point $N_p$ may be about 5 points to about 10 points.

The value of the point $P_{int}[j]$ or $P_{ext}[j]$ includes a vector that designates the location of this point in the 3D stack I or $I_r$. For example, $P_{int}[5]$ refers to the fifth point on the internal contour of a capillary. The value of $P_{int}[5]$ may be, for example (20, 30), which indicates the 2D location of the point on the image, i.e., twentieth row and thirtieth column. After acquiring the 2D location of this point on the curve, the pixel value (or intensity) of the pixel may be retrieved from the image stack I or $I_r$. In this way, index on the curve (j), pixel location (k), and pixel value are correlated to each other in a one-to-one manner.

Resampling of Capillary Contour Points

The contour points specified, for example, at step 220 of method 200, are usually sparse and may only mark, for example, certain characteristic points on the internal and external boundaries of capillaries (e.g., starting point, ending point, or turning points). Therefore, at step 230 of method 200, the specified internal and external contour points are resampled so as to further refine the boundaries for further processing in accordance with some embodiments.

At least one of three methods and/or a combination thereof may be used to resample the specified contour points. In some embodiments, interpolation (e.g., linear interpolation, polynomial interpolation, or spline interpolation) is used to generate new data points between two adjacent specified points so as to fill the gap. In some embodiments, curve fitting (e.g., using linear or nonlinear regression) is used to fit the specified contour points to a curve, which generally has an analytic expression and therefore can contain an arbitrary number of data points for further processing. In some embodiments, extrapolation (e.g., using linear extrapolation, polynomial extrapolation, conic extrapolation, or French extrapolation) is employed to generate projected points beyond the curve section defined by the specified contour points. In further embodiments, a combination of two or more these methods is used.

In some embodiments, a denser set of points $P'_{int}$ and $P'_{ext}$ is generated using cubic-spline interpolation of the original points with a resampling factor $\alpha$. The total number of contour points after resampling is therefore $\alpha(N_p-1)+1$, where $N_p$ is the number of contour points specified. The resampling factor $\alpha$ may be at least partially dependent on the desired resolution of the resampled contours, i.e., the distance between two adjacent resampled contour points (also referred to as point spacing). For example, if WBC events are to be detected, it is preferred to set the point spacing smaller than the size of WBCs so as to resolve each WBC in subsequent processing. In some embodiments, the point spacing may be substantially similar to the pixel size in the source images in the capillary data.

Figure 4A:
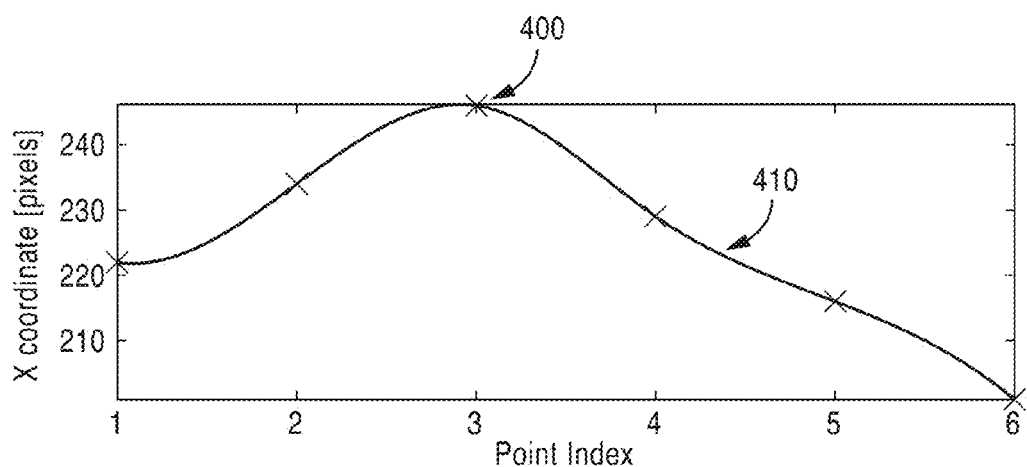
FIGS. 4A-4B are plots of cubic spline interpolation that can be used in the methods illustrated in FIGS. 1-2 for resampling user-specified contour points of capillaries in accordance with some embodiments.
Figure 4B:
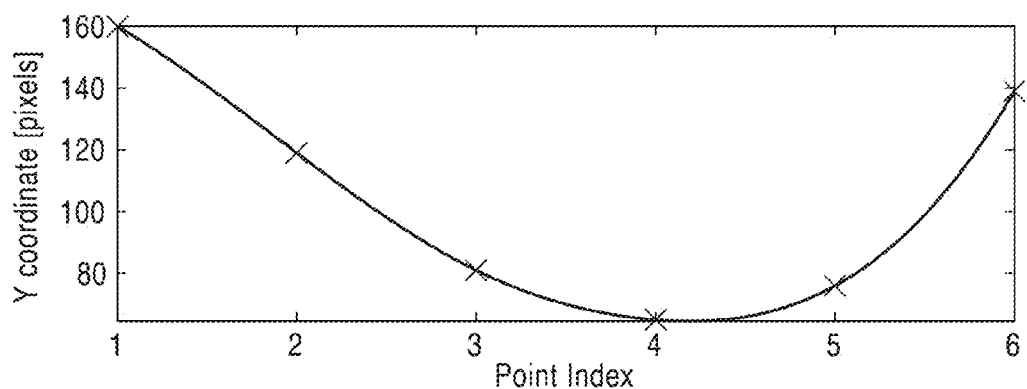

In some embodiments, resampling is performed directly on the 2D coordinates specified at step 220. For example, 2D spline (also referred to as bicubic interpolation) may be used to resample the specified contour points. In some embodiments, the point-resampling operation at step 230 includes separate 1D resampling of the corresponding horizontal and vertical coordinate sequences (also referred to as row and column sequences, respectively). FIG. 4A is a plot of a cubic spline interpolation of x-coordinates, and FIG. 4B is a plot of a cubic spline interpolation of y-coordinates. In FIGS. 4A-4B, the contour points specified at step 220 are marked as crosses (e.g., cross 400) and the resampled contour points connect the crosses. Note that the resampled data points are so numerous that they appear as continuous curves (e.g., apparent curve 410).

Definition of Intermediate Curves and Curvilinear Distances

At step 240 of method 200, a series of intermediate curves are defined between the internal contour and the external contour of each identified capillary according to some embodiments. In some embodiments, the series of intermediate curves are evenly distributed in the space defined by the internal and external contours. In some embodiments, the distribution of intermediate curves is uneven. For example, the central portion of the capillary may have a higher density of intermediate curves compared to an edge portion of the capillary.

In some embodiments, a series of $N_c$ intermediate curves $P'_m[j]$ is generated by linear combinations of the form:

$$tP'_{int}+(1-t)P'_{ext} \quad (4)$$

where $m=1, 2, \ldots, N_c$, $N_c$ is the total number of intermediate curves; $j=1, 2, \ldots, \alpha(N_p-1)+1$, $\alpha(N_p-1)+1$ is the total number of data points in each curve; and $t=(m-1)/(N_c-1)$ is a linear combination coefficient.

The total number of intermediate curves $N_c$ may be dependent on the desired resolution of the collection of intermediate curves, i.e., the distance between two adjacent intermediate curves (also referred to as curve spacing). For example, if WBC events are to be detected, the curve spacing may be set smaller than the size of WBCs so as to resolve each WBC in subsequent processing. In some embodiments, the curve spacing may be substantially similar to the pixel size in the source images in the capillary data.

The resampling of contour points at step 230 may be regarded as improving the longitudinal resolution (i.e., the resolution along the direction of the capillary) from specified contour points at step 220. The creation of intermediate curves, on the other hand, may be regarded as improving the lateral resolution (i.e., the resolution along the cross-section of the capillary) based on two boundaries (i.e., the internal and external contours) of the capillary.

In some embodiments, step 230 is performed before step 240 such that intermediate curves can be created based on the resampled contour points acquired at step 230. In some embodiments, step 240 is performed before step 230. For example, a series of intermediate points may be created between one user-specified point on the internal contour and one user-specified point on the external contour so as to fill gaps along the cross-section of the capillary. The same step may be performed for each pair of user-specified points, thereby generating a series of sets of intermediate contour points between the internal contour points and the external contour points. Then a resampling step, like the one at step 230, may be performed for each set of intermediate contour points to string together the intermediate contour points, thereby generating a series of intermediate curves.

At step 240, a middle curve $P'_{mid}$ may be defined as:

$$P'_{mid}=\tfrac{1}{2}P'_{int}+\tfrac{1}{2}P'_{ext} \quad (5)$$

This middle curve $P'_{mid}$ may be used to define curvilinear distances. Curvilinear distance may be defined as the Euclidian norm between each point in $P'_{mid}[j]$ with respect to the starting point $P'_{mid}[1]$. In some embodiments, for simplicity, the jth data points on different intermediate curves $P'_m[j]$ are assigned the same curvilinear distances as $P'_{mid}[j]$.

Figure 5:
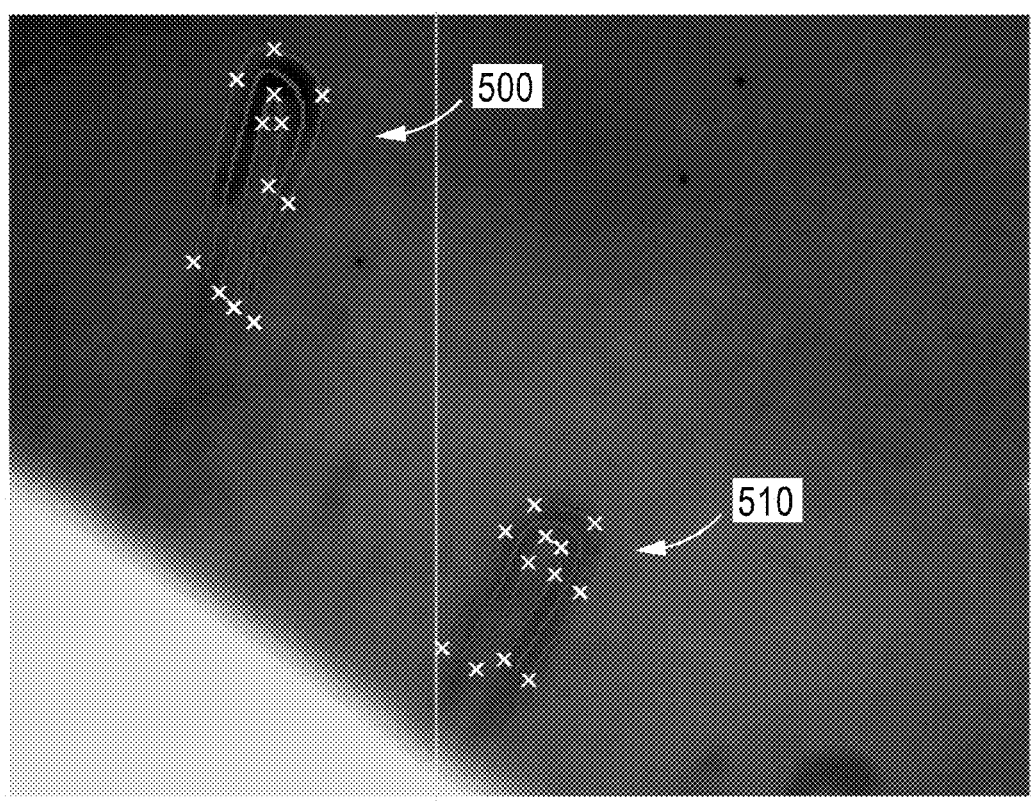
FIG. 5 is an image of a nailfold including two capillaries, user-specified contour points, and resampled contour curves in accordance with some embodiments.

FIG. 5 is a normalized and registered image frame $I_r$ from a video clip including capillary 500 and capillary 510. Both capillaries are highlighted in the processed image along with the corresponding user-defined contour points (shown as crosses) and interpolated points (shown as curves) that follow the internal and external curves of each profile. The middle curve $P'_{mid}$ from which the curvilinear distances are computed is also shown. Note that the user has specified only six points and yet the resampled curves already appear to be in good agreement with the actual boundaries of the two capillaries.

Intensity Profile Extraction

At step 260 of method 200, the intensities of the pixels (i.e., pixel values) within the capillary segments are extracted as a function of curvilinear distance so as to form a spatiotemporal profile f[j; m; l], wherein j is the curvilinear index (the jth point on certain curve), m is the curve index (the mth curve in the plurality of curves including the internal boundary, the external boundary, and the intermediate curves generated in between), and l is the frame index (the lth image in a sequence of images). More specifically, each $P'_m[j]$ on $I_r$ is associated with an intensity value. In some embodiments, bilinear interpolation is used to compute the resulting intensities f[j; m; l] with sub-pixel precision at given curvilinear index j, curve m, and frame l.

In some embodiments, given f[j; m; l], the average of the capillary intensities of all curves can be computed for every frame and curvilinear distance so as to generate an averaged spatiotemporal profile f'[j; l] (i.e., averaged over all m from 1 to $N_c$). As an analogy, this averaging step can be regarded as collapsing all capillary curves (internal contour, external contour, and intermediate curves) into a single curve.

In some embodiments, the averaged spatiotemporal profile f'[j; l] is resampled to generate a resampled spatiotemporal profile g[j; l], which contains the same number of samples as f'[j; l] but with equidistant curvilinear spacing. The resampling may be performed using linear interpolation.

Spatiotemporal Profile Analysis

The profile g[j; l] may include an intensity profile evolving as a function of time for each point j along the curvilinear distance of each capillary. This profile can exhibit correlations in space and time, which may be extracted to overcome possible challenges in analyzing noisy source images taken at relatively low-frame-rate and/or with low-resolution.

In some embodiments, to emphasize the intensity variations created by WBC events, a median-normalized version of g is computed. More specifically, the medians of the time-varying intensity lines of g[j; l] may be first set to zero at every curvilinear coordinate j. Then the same operation may be performed column-wise at every frame l. To reduce noise, the contrast-normalized profile g' may be filtered along the time axis with a symmetric and unit-sum rectangle function of size σ, which yields g''. The filtering operation may be performed through convolution with said rectangle function.

Figure 6A:
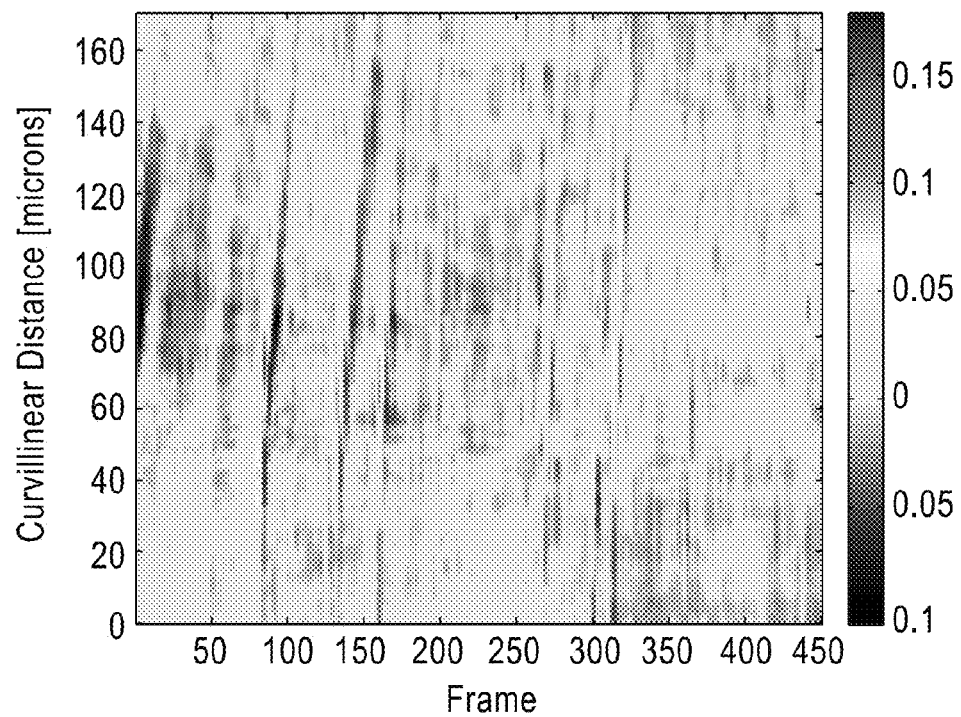
FIGS. 6A-6B are representations of spatiotemporal profiles extracted from the two capillaries shown in FIG. 5 in accordance with some embodiments.
Figure 6B:
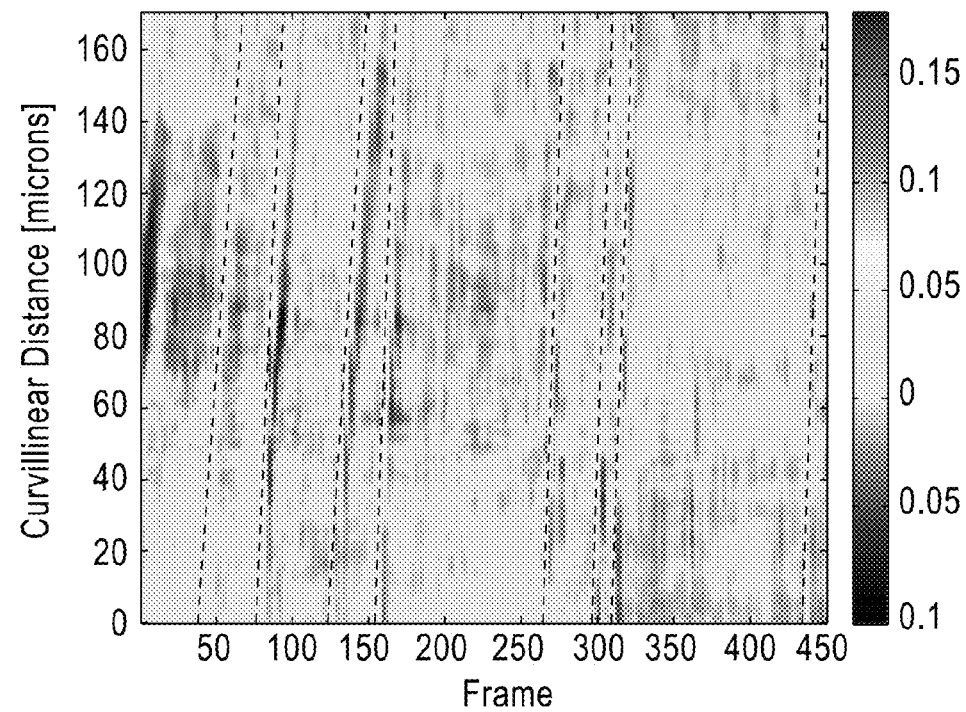

FIG. 6A shows an example spatiotemporal profile g'' of capillary 500 from FIG. 5. The spatiotemporal profile g'' was generated based on the original spatiotemporal profile f[j; m; l], after averaging over all m from 1 to $N_c$ (achieve f'[j; l]), resampling to have equidistant curvilinear spacing (achieve g[j; l]), median-normalization (to achieve g'[j; l]), and filtering (to achieve g''[j; l]). On the spatiotemporal profile shown in FIG. 6A, spatiotemporal trajectories corresponding to WBC events can be identified. FIG. 6B illustrates these trajectories by dashed lines spanning the 2D intensity plot. The slope of each line may be associated with the average speed of the corresponding WBC event inside the capillary. Therefore, the spatiotemporal profiles like those shown in FIGS. 6A-6B already provide important information about WBC events in the capillaries such as the number of events and the flow speed. This information may be extracted manually, automatically, or semi-automatically using the methods described above.

Radon Transform

At step 270 of method 200, a Radon transform is performed on the spatiotemporal profiles generated in step 260 according to some embodiments. The Radon transform maps 2D lines to peaks located at particular positions so as to identify events and their associated parameters. Event detection using Radon transform is not only convenient but robust to noise.

Without being bound by any particular theory or mode of operation, given a continuous 2D image f(x), wherein x is a 2D Cartesian coordinate defined with respect to the center of the image f(x), the Radon transform called f̂=Rf may be defined as $$\hat{f}(\theta, x_1') = \int_{-\infty}^{\infty} f(x_1' \cos\theta - x_2' \sin\theta, x_1' \sin\theta + x_2' \cos\theta) dx_2' \quad (6)$$

where the radial coordinate x' is defined as x'=[$x_1 \cos\theta + x_2 \sin\theta$, $-x_1 \sin\theta + x_2 \cos\theta$].

In some embodiments, f(x) is a discrete image, in which case a discrete-domain Radon transform $R^0$ involving a finite amount of radial-coordinate values and of angles in [0; π] may be used. The largest radial-coordinate value can correspond to half of the image-diagonal length. The profile in Radon-domain ĝ is thus represented as:

$$\hat{g}[k_\theta, k_r] = R^0 g'' \quad (7)$$

The number of angles is denoted by $N_\theta$, the number of radial coordinates $N_r$ being proportional to $(N_f^2 + N_{p,i}^2)^{1/2}$, where $N_{p,i} = \alpha(N_p - 1) + 1$ is the number of interpolated curvilinear points.

Figure 7:
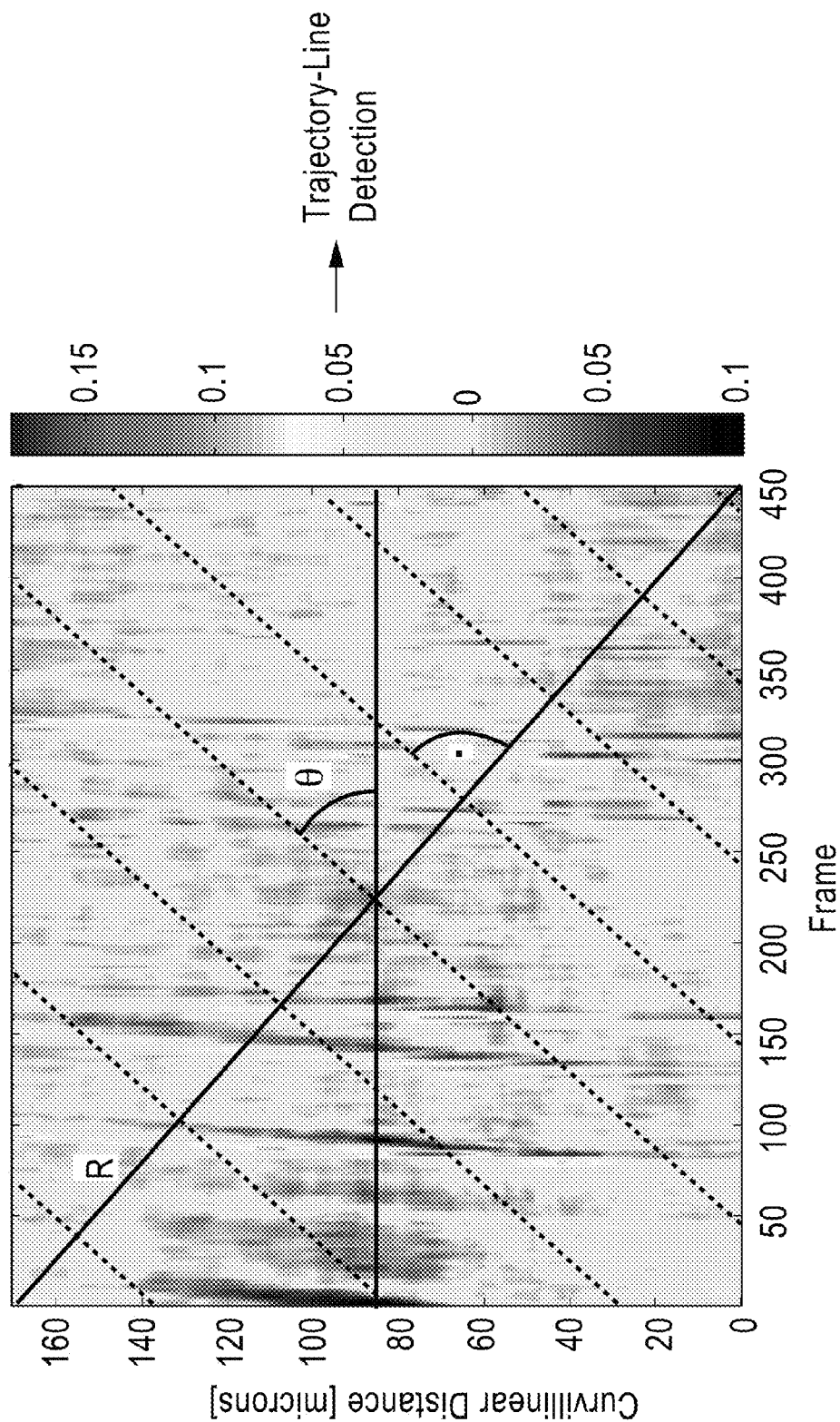
FIG. 7 is a representation of a Radon transform performed on a spatiotemporal profile in accordance with some embodiments.

FIG. 7 illustrates the application of the Radon transform on the spatiotemporal profile shown in FIGS. 6A-6B according to some embodiments. The projection angle θ and radial coordinate R are shown in FIG. 7. The solid arrow illustrates the direction for trajectory-line detection. Considering a predefined set of angles θ and radial coordinates R, the Radon transform computes projections of the spatiotemporal-profile intensities (i.e., the intensities in the non-transformed domain, as shown in FIG. 7). More specifically, the Radon-transformed-domain value (see FIG. 8A) for a given angle θ and radial coordinates R corresponds to the integral of all values (i.e., the intensity values in the non-transformed domain, as shown in FIG. 7) that are found on the line whose counterclockwise angular inclination with respect to the horizontal axis is θ and whose radial coordinate is R.

Figure 8A:
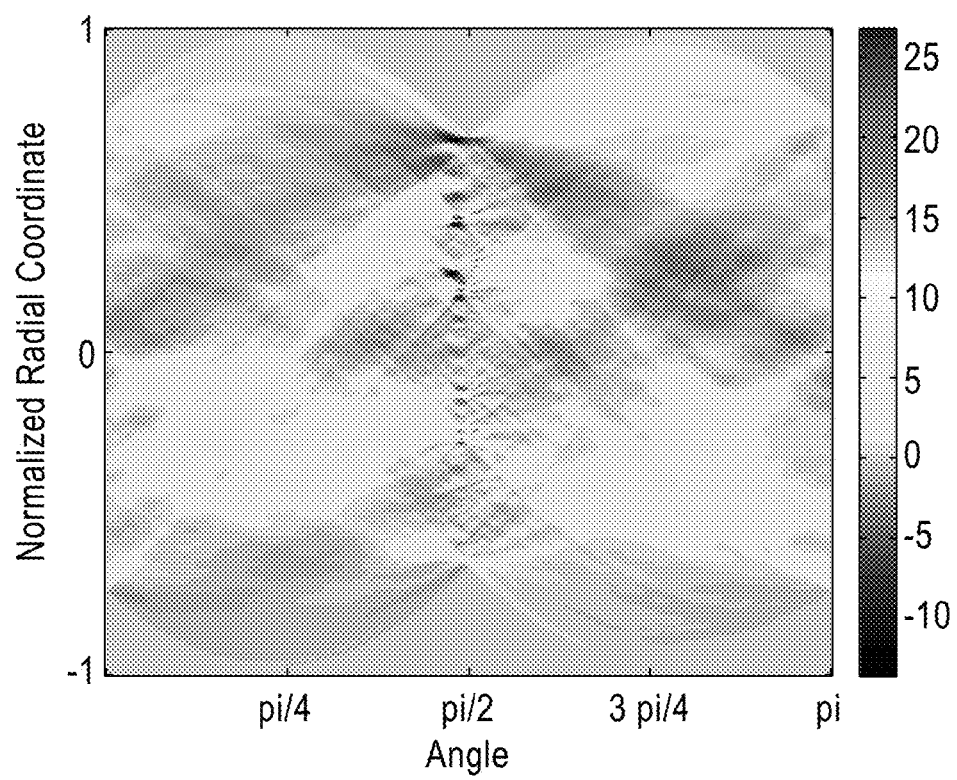
FIGS. 8A-8B are representations of spatiotemporal profiles in the Radon domain with local maxima highlighted to indicate WBC events in accordance with some embodiments.

FIG. 8A shows the Radon transform ĝ of the map in FIG. 7 according to some embodiments. The horizontal and vertical axes correspond to the projection angle and to the associated normalized radial coordinate, respectively. In FIG. 8A, several peaks may be readily identified. Each peak may correspond to the linear trajectories observed in the spatial domain (e.g., FIG. 6B). These peaks may be identified and located based on, for example, local-maxima detection within a window of odd pixel size $S_w \times S_w$. In some embodiments, the local-maxima are limited to those greater than a threshold $\tau_m$. In some embodiments, the maxima locations are limited to locations with angular values within the range [0; π/2], thereby imposing one single flow direction inside the capillary.

Figure 8B:
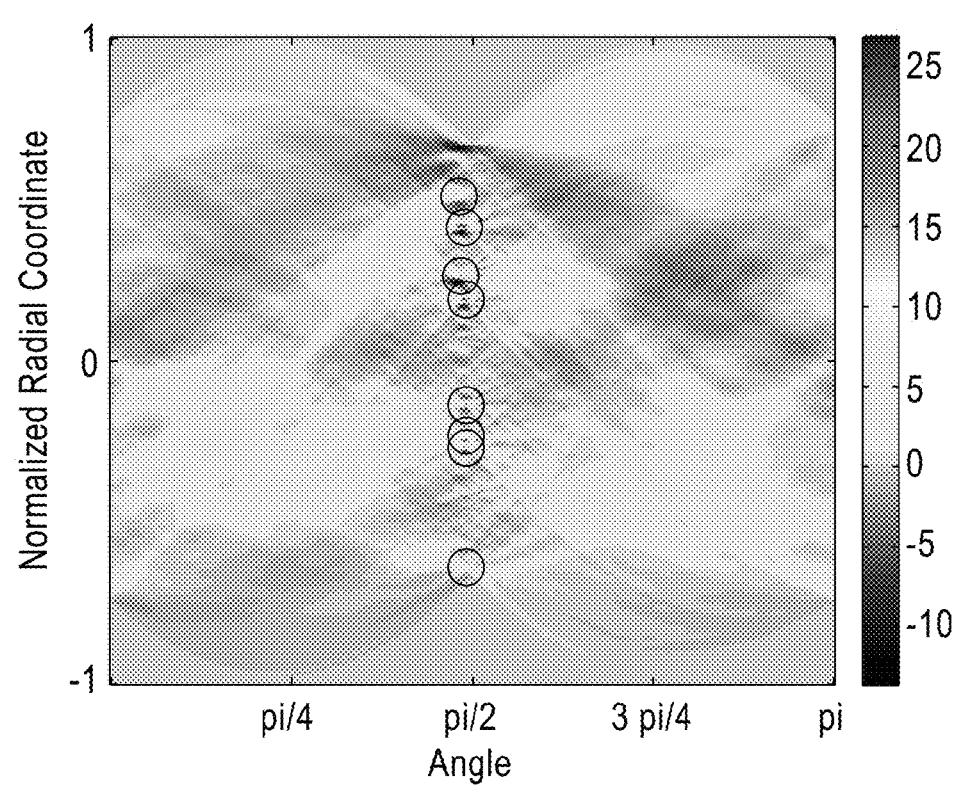

FIG. 8B shows the spatiotemporal profile in the Radon domain with identified peaks highlighted in circles. The original physical time and speed parameters of WBC events in the capillaries may be analytically deduced from the maxima locations based on the known frame rate and pixel size through elementary trigonometric relations. More specifically, the speed is associated with the tangent of the projection angle θ in the Radon domain, and is thus proportional to the vertical slope of the corresponding trajectory line in the aforementioned spatiotemporal profile g''. The original physical time is associated with the intersection between said trajectory line and the time axis of said spatiotemporal profile. In some embodiments, the time of each WBC event corresponds to the first frame in which a visual gap appears in the capillary.

EXAMPLES

Figure 9A:
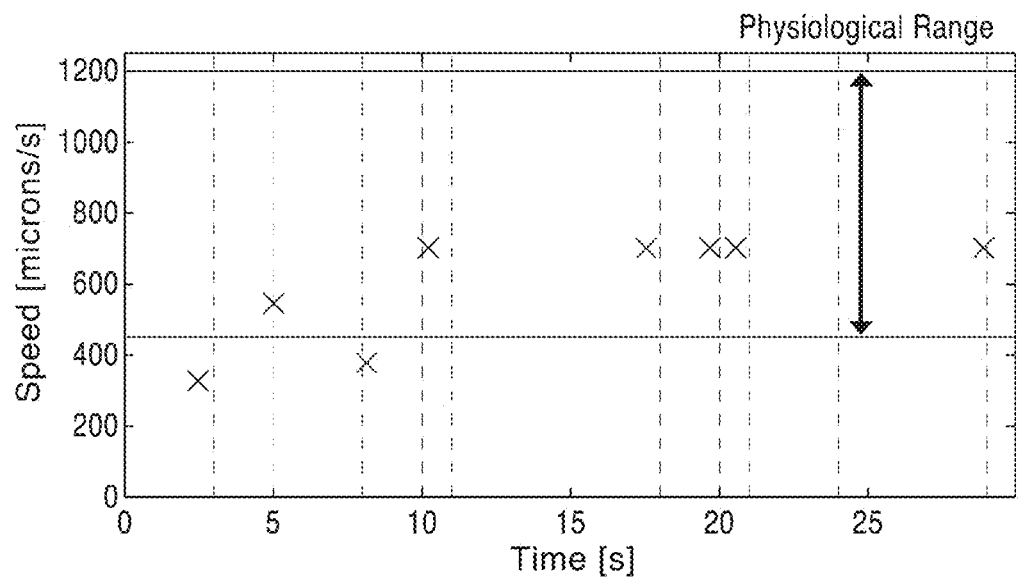
FIGS. 9A-9B are plots representing experimental results of WBC events occurring inside the two capillaries shown in FIG. 5 in accordance with some embodiments.
Figure 9B:
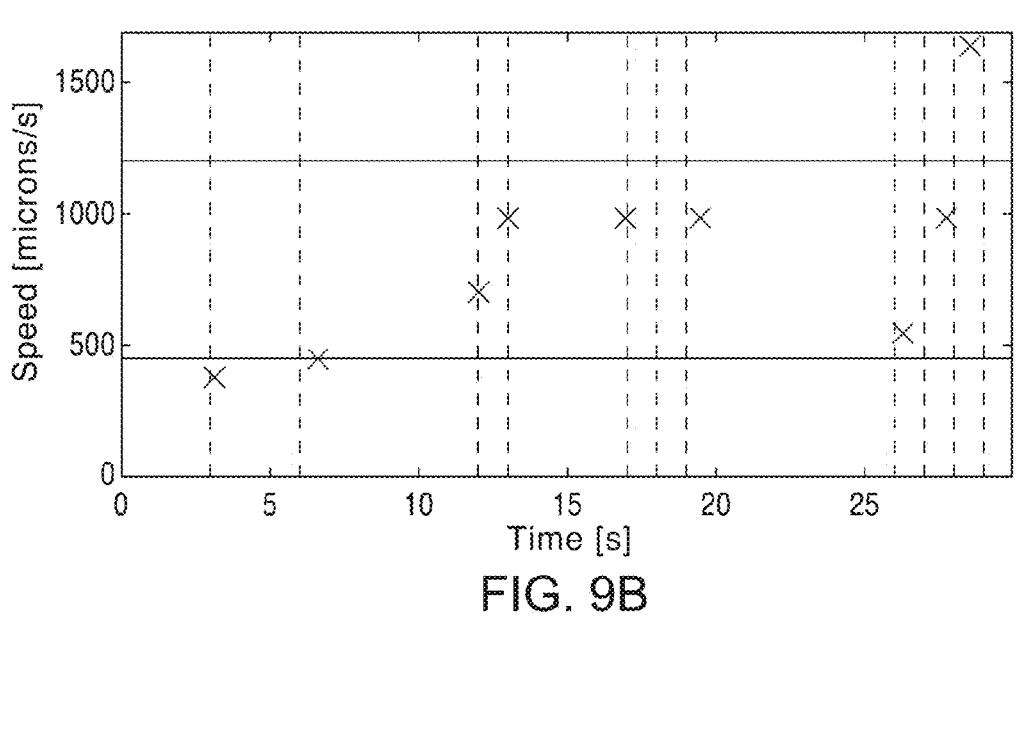

FIG. 9A shows experimental results of WBC events occurring inside capillary 500, and FIG. 9B shows experimental results of WBC events occurring inside capillary 510 shown in FIG. 5 according to some embodiments. The experimental results are compared to manual counts performed by four trained human reviewers. In FIGS. 9A-9B, WBC events detected by the methods described above are marked by a cross, while the event times estimated by a trained human reviewer are denoted by the dashed vertical lines. The horizontal lines represent the maximum and minimum blood-flow-related limits.

The source images are taken from a video clip of a human nailfold. The acquisition parameters are $N_h=1280$, $N_v=960$, $N_f=450$, $r=15$, and $S_p=0.65$ µm, the duration of the video clip is 30 s. The threshold $\tau_c$ is heuristically set to ¾ of the maximum intensity value for each frame l in I'. The amount of user specified curve points is set to $N_p=6$, which can yield accurate segmentations. The number of interpolated curves is set to $N_c=10$, using $\alpha=100$ for resampling. The size of the filter used for noise reduction is set to $\sigma=3$. Finally, the window size and threshold value used for Radon-domain maxima detection are selected as $S_w=11$ and $\tau_m=7$, the number of Radon angles being set to $N_\theta=400$.

In FIGS. 9A-9B, more than 80% of the WBC events detected by the methods described above are consistent with those of a trained human reviewer. Missed events may correspond to temporally adjacent visual gaps that can be challenging for automatic methods to resolve due to the poor frame rate.

Figure 10:
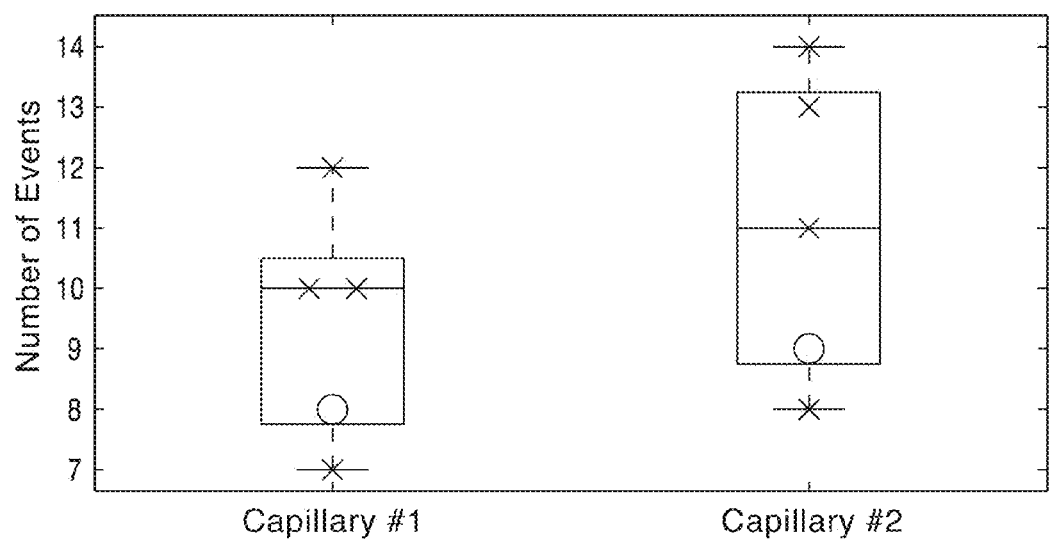
FIG. 10 is a plot comparing WBC events obtained from methods illustrated in FIG. 2 in accordance with some embodiments and WBC events identified by trained human reviewers.

FIG. 10 shows a further comparison between the total WBC event counts obtained from methods described above in accordance with some embodiments and those obtained from all four trained human reviewers. FIG. 10 also shows significant inter-observer variability of manual counts. Each capillary is associated with a box where the central mark is the median. The edges of the box are the 25th and 75th percentiles, and the whiskers extend to the extreme data points. The crosses and the circles denote the counts completed by each of the four trained human reviewers and by our algorithm, respectively. The results obtained from the described methods are shown in these box plots to fall within the human inter-rater variability.

The slope of the visual gap trajectories in FIGS. 6A-7B may be employed to compute the speed associated with WBC events for both capillary 500 and capillary 510. The results, represented in FIGS. 9A-9B, fall within the range for blood-flow values of human nailfold capillaries previously reported in literature, that is, about 450 µm/s to about 1200 µm/s.

Interpolated inner and outer capillary curves, $P_{int}[j]$, $P_{ext}[j]$ may be employed to extract the vessel radius r, which corresponded to approximately 7.5 µm for both capillary 500 and capillary 510, a value consistent with previous published data.

Without being bound any particular theory or mode of operation, capillaries may be assumed to have circular cross-sections. Given that the average speed v derived above is approximately 600 µm/s, the total sampled blood volume per second V may be determined as:

$$V = \pi v r^2 = \pi \cdot 600 \frac{\mu m}{s} \cdot (7.5 \mu m)^2 \approx 105 \cdot 10^{-6} \frac{\mu L}{s} \quad (8)$$

Given that a healthy WBC range is about 3500 WBCs per µL to about 9000 WBCs per µL, and given that the duration of the video clip is 30 seconds, a number c of WBC counts may be determined as:

$$c = [3.5, 9] \cdot 10^3 \frac{wbc}{\mu L} 105 \cdot 10^{-6} \frac{\mu L}{s} \cdot 30s \approx [11, 28] wbc \quad (9)$$

which is consistent with the median counts of ten WBC events and eleven WBC events obtained for capillary 500 and capillary 510, respectively.

Figure 11A:
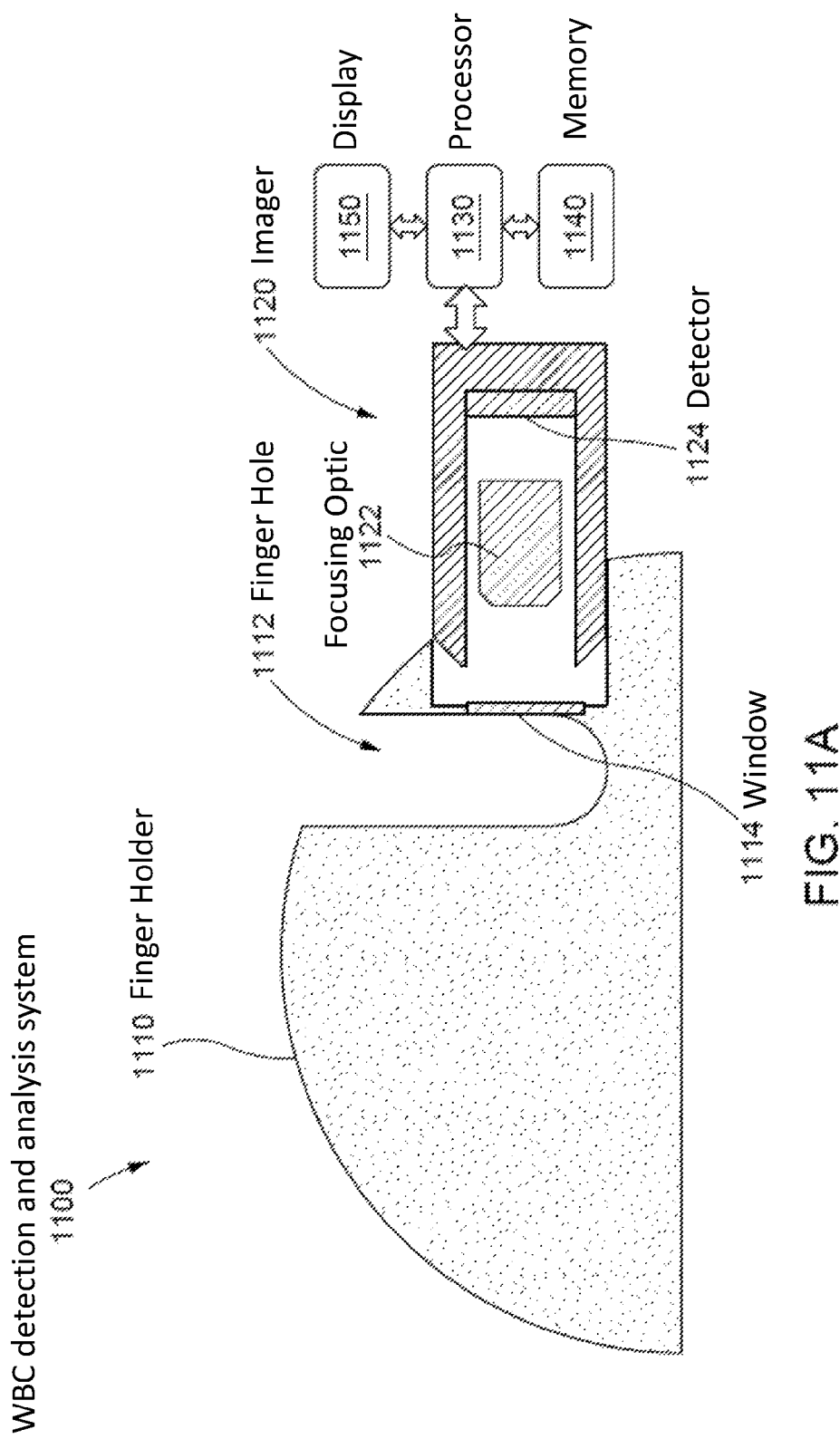
FIGS. 11A-11C are schematics of systems for analyzing blood cell dynamics using a finger holder and an imager in accordance with some embodiments.
Figure 11B:
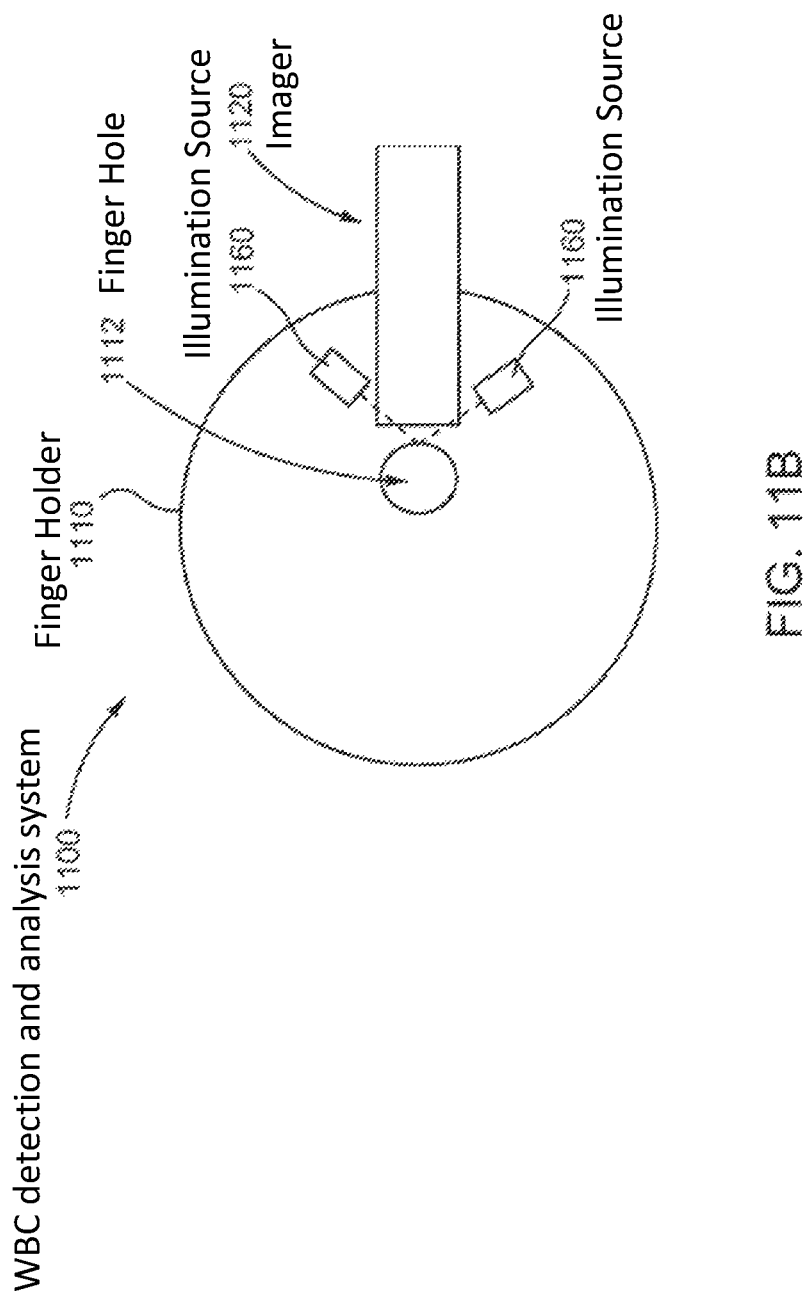

Apparatus and Systems for Non Invasive and In Vivo Analysis of Blood Cell Dynamics FIGS. 11A-11B are schematics of a system for detecting white blood cell (WBC) events in an in vivo and non-invasive manner according to some embodiments. FIG. 11A is a side view of the system, and FIG. 11B is a top view of the system. For purposes of illustration, embodiments described herein analyze WBC events in a human nailfold; however, the embodiments may be modified for analysis in other subjects and/or other locations in or on the body of a subject. In FIGS. 11A-11B, system 1100 includes finger holder 1110 having finger hole 1112 to receive at least a portion of a human finger (e.g., a nailfold portion of the finger). Finger holder 1110 is also configured to receive imager 1120, which is in optical communication with the finger received by finger hole 1112 through transparent window 1114 so as to capture images or videos of the finger. The imager further includes focusing optic 1122 to collect light reflected or scattered from the finger and detector 1124 to receive the reflected or scattered light so as to form images of the finger. System 1100 further includes processor 1130 operably coupled to imager 1120 and memory 1140 operably coupled to processor 1130. Memory 1140 is encoded with processor-executable instructions, which, when executed by processor 1130, may perform the methods described above to analyze images received from imager 1120. System 1100 also includes display 1150, which can display the images or videos taken by imager 1120 and/or data associated with WBC events detected by processor 1130.

In some embodiments, finger holder 1110 has an igloo shape (as shown in FIGS. 11A-11B) such that the hand can rest on the dome of the finger holder while a finger in the hand is received by finger hole 1112 for imaging. Finger holder 1110 may have other configurations such as a flat top, a handle configuration (the hand can grip the handle while a finger can be imaged), or any other configurations known in the art.

In some embodiments, system 1100 also includes illumination source 1160 (shown in FIG. 11B) to illuminate the finger and facilitate image taking by imager 120. In some embodiments, illumination source 1160 includes a pair of light emission diodes (LEDs), each of which is disposed on one side of finger hole 1112. In some embodiments, illumination source 1160 is configured to emit monochromatic light. Capillary structures in the finger can have a high reflectivity at the wavelength of the monochromatic light.

Figure 11C:
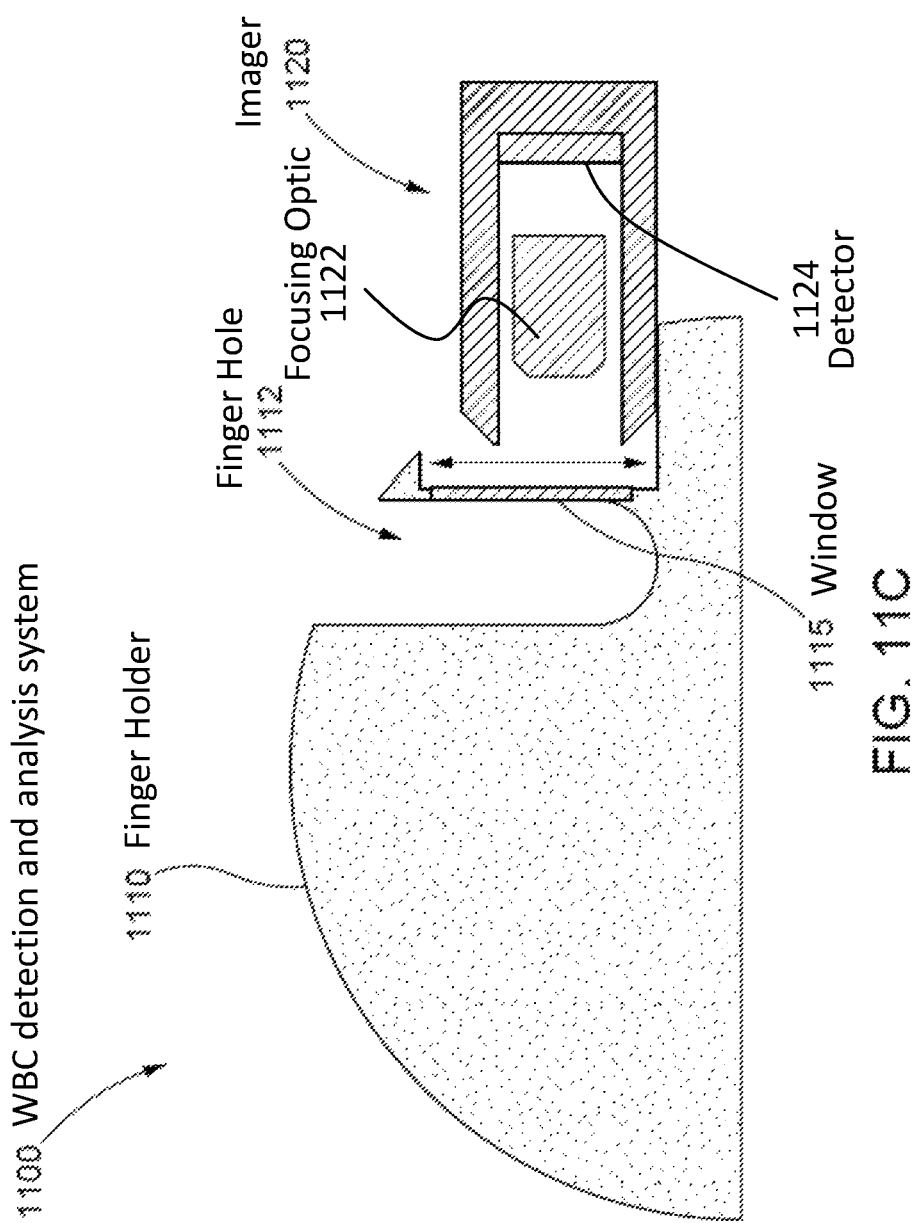

FIG. 11C shows a schematic of a system 1100 substantially similar to the system shown in FIGS. 11A-11B in accordance with some embodiments. The system 1100 includes an adjustable transparent window 1115 disposed between finger hole 1112 and imager 1120. By adjusting the height of window 1115, imagers 1120 having different sizes may be used to capture images of the finger.

Figure 12A:
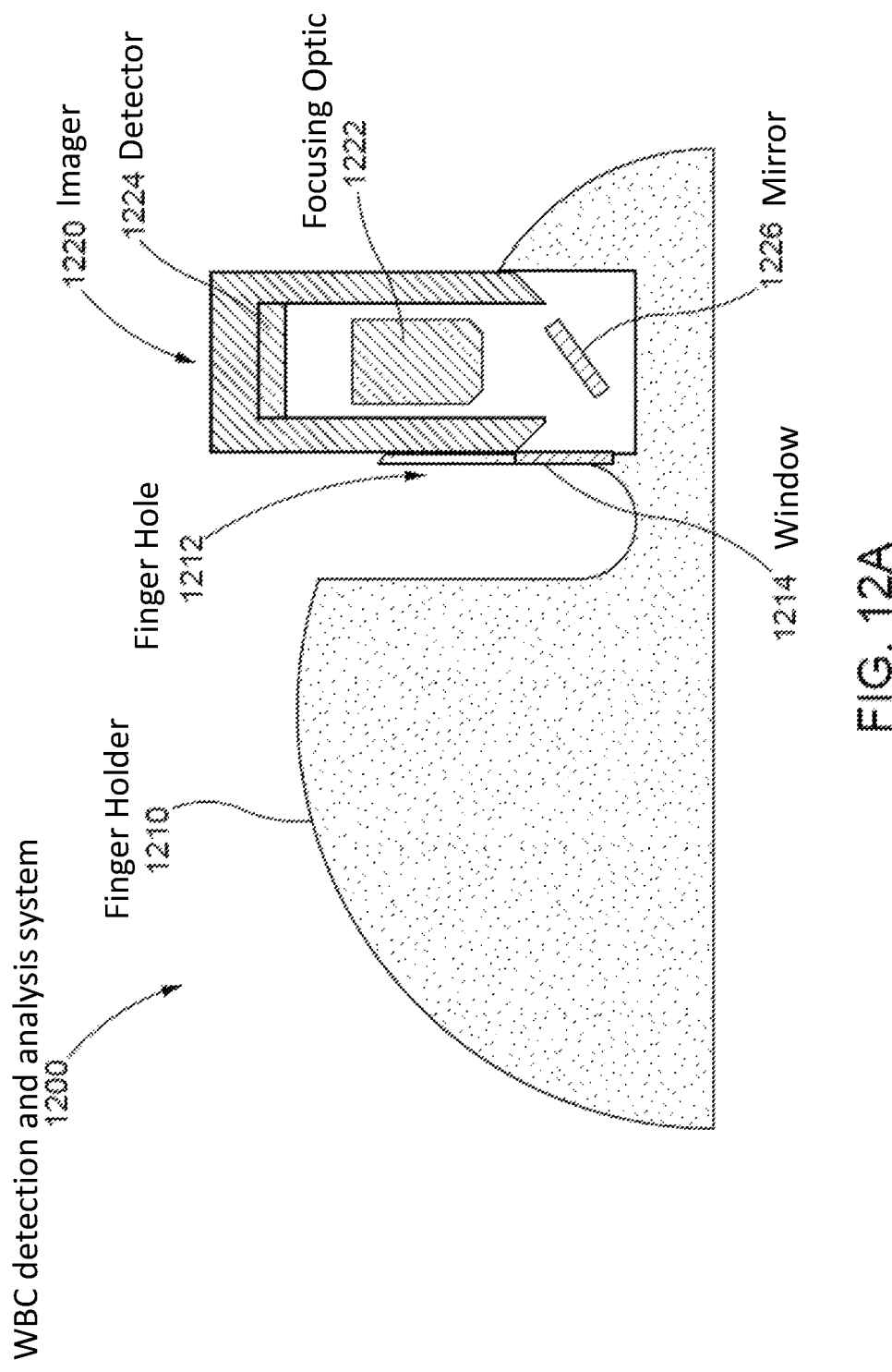
FIGS. 12A-12B are schematics of systems for analyzing blood cell dynamics using an imager in vertical configuration in accordance with some embodiments.
Figure 12B:
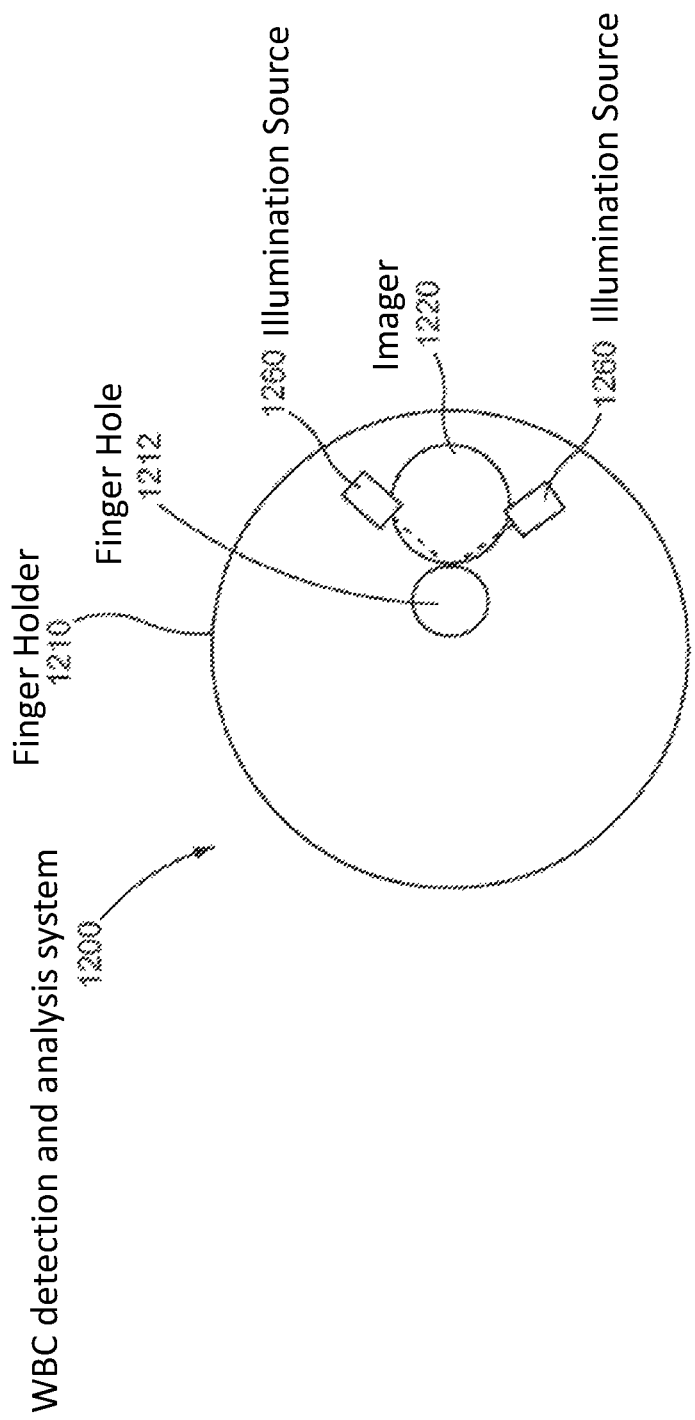

FIGS. 12A-12B are schematics of an system for capturing in vivo images for non-invasive analysis of WBC events according to some embodiments. FIG. 12A is a side view of system 1200, and FIG. 12B is a top view of system 1200. System 1200 includes finger holder 1210 having finger hole 1212 to receive at least a portion of a human finger (e.g., a nailfold portion of the finger). Finger holder 1210 is also configured to receive imager 1220, which is in optical communication with the finger received by finger hole 1212 through transparent window 1214 and mirror 1226 so as to take images or videos of the finger. The imager further includes focusing optic 1222 to collect light reflected or scattered from the finger and detector 1224 to receive the reflected or scattered light so as to form images of the finger. In system 1200, imager 1220 is disposed in a vertical configuration. Mirror 1226 is configured to reflect the image of the finger toward imager 1220. In some embodiments, mirror 1226 is coupled to an actuator (not shown), which can tilt mirror 1226 in two directions. The tilting may help imager 1220 point at the desired portion of the finger for imaging. Similar to system 1100, system 1200 also may have an illumination source 1260 to facilitate capturing images by imager 1220.

Figure 13:
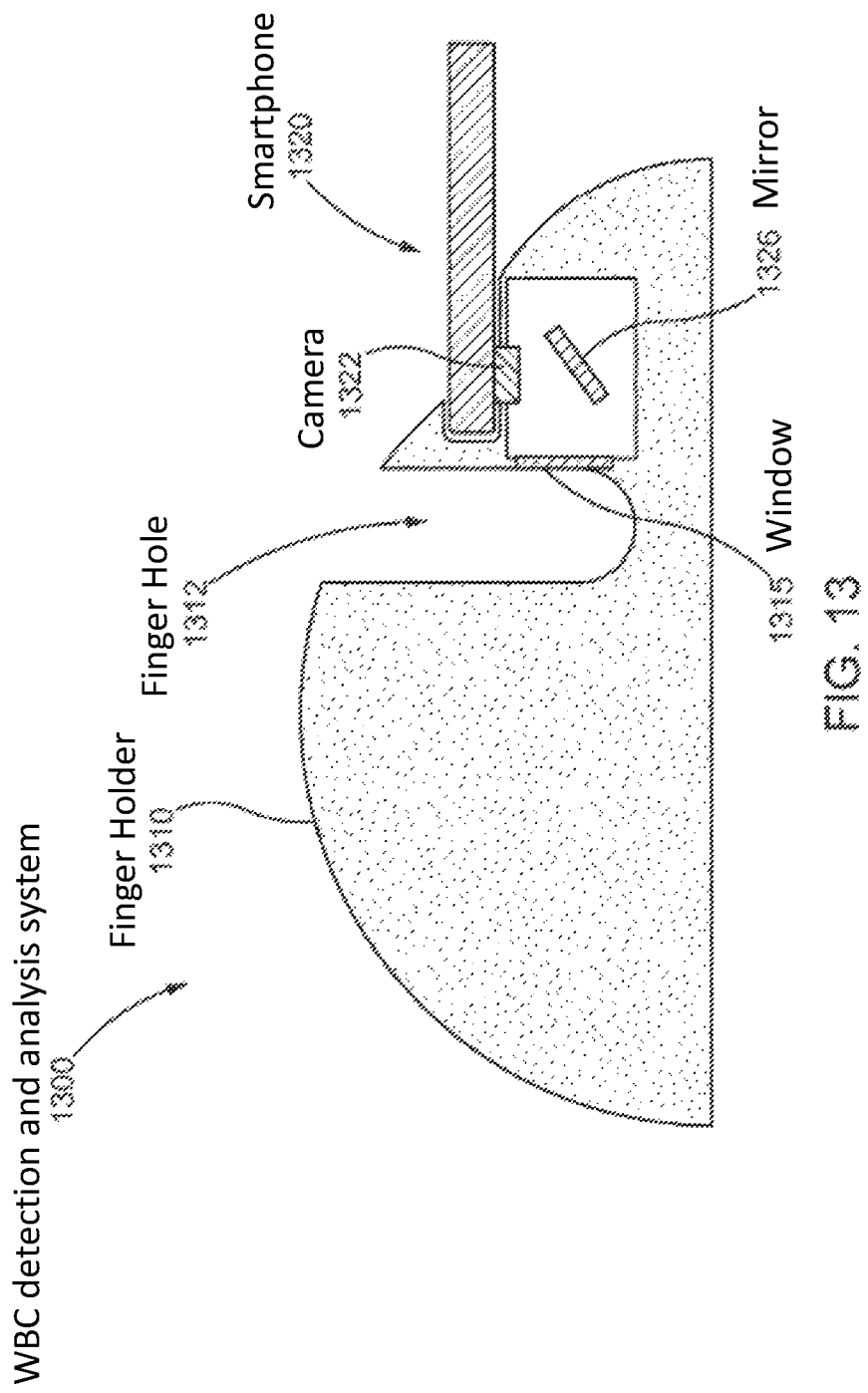
FIG. 13 is a schematic of a system for analyzing blood cell dynamics analysis using a smartphone in accordance with some embodiments.

FIG. 13 is a schematic of a system for performing in vivo and non-invasive analysis of blood cell dynamics using a camera-equipped device (e.g., a smartphone) according to some embodiments. System 1300 includes finger holder 1310 having finger hole 1312 to receive at least a portion of a finger for imaging. Finger holder 1310 is also configured to receive smartphone 1320 such that the camera in smartphone 1320 is in optical communication with the finger in finger hole 1312 via transparent window 1315 and mirror 1326. System 1300 also may include modifying optic 1322, disposed in front of the camera in smartphone 1320, so as to adapt smartphone 1320 for better image capture. For example, modifying optic 1322 may include a lens to adjust the focal length (optical zooming) of the camera in smartphone 1322. Cameras in many smartphones do not have optical zooming, thus including lens 1322 may increase the optical flexibility of the camera. The focal length of the camera is also related to the resolution of the images captured by the camera. Therefore, use of lens 1322 also may adjust the resolution of the images for further processing.

Smartphone 1320 generally includes its own memory and processor. Methods described in earlier sections of this application can be encoded as processor executable instructions into the memory of smartphone 1320. In operation, images taken by the camera may be transmitted to the processor for the analysis of blood cell dynamics. In some embodiments, images taken by the camera are transmitted wirelessly (e.g., via Bluetooth, WiFi, 3G network, 4G network, or any other wireless communication protocols known in the art) to another processor for processing. In some embodiments, images taken by the camera are locally saved into the memory of smartphone 1320.

Figure 14A:
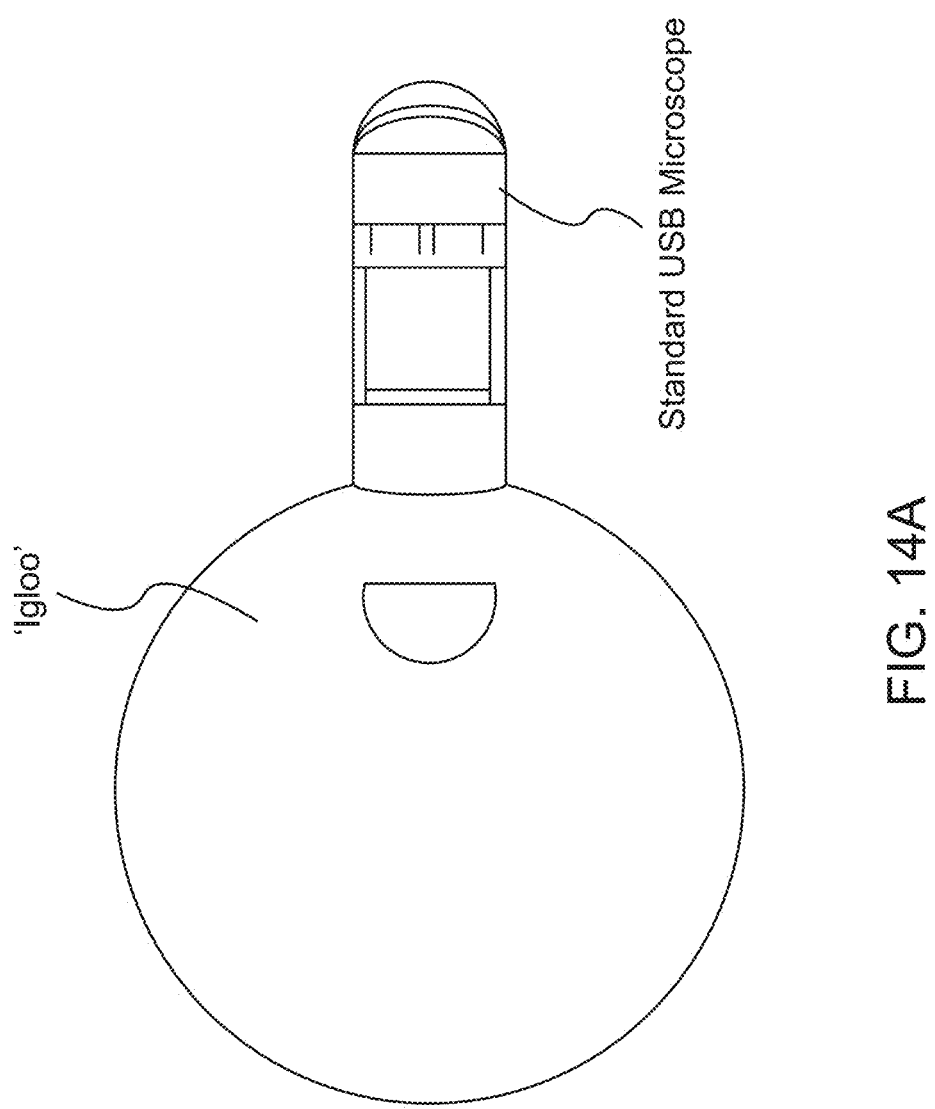
Figure 14C:
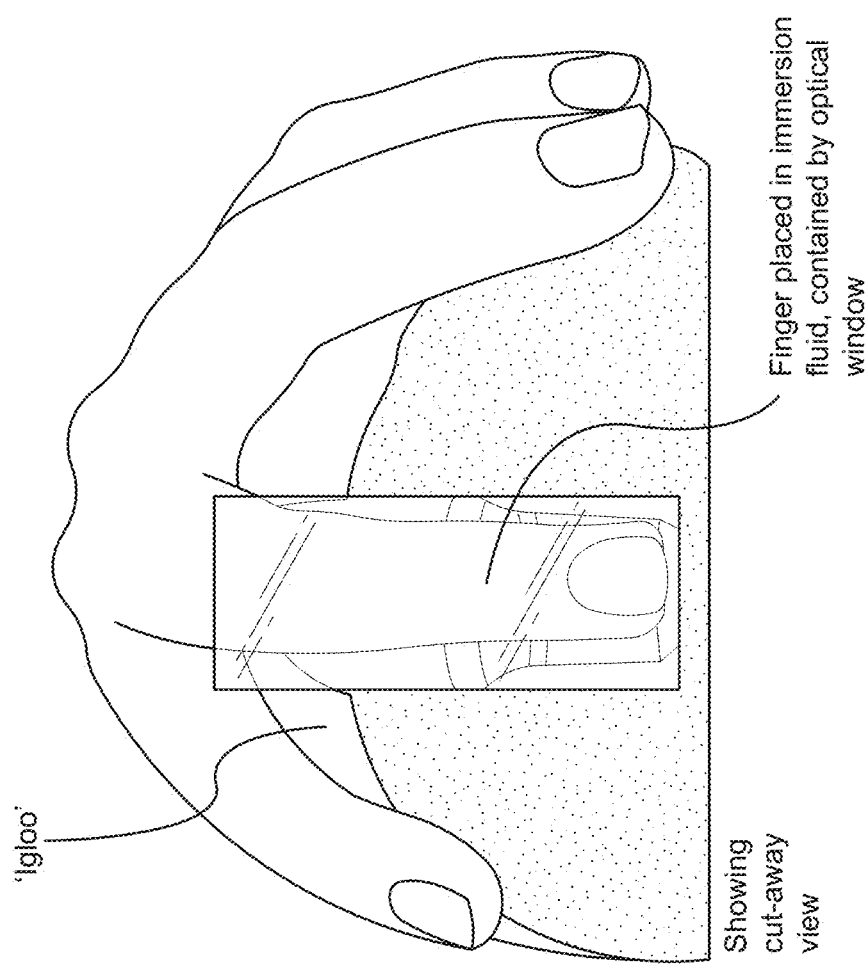
Figure 14D:
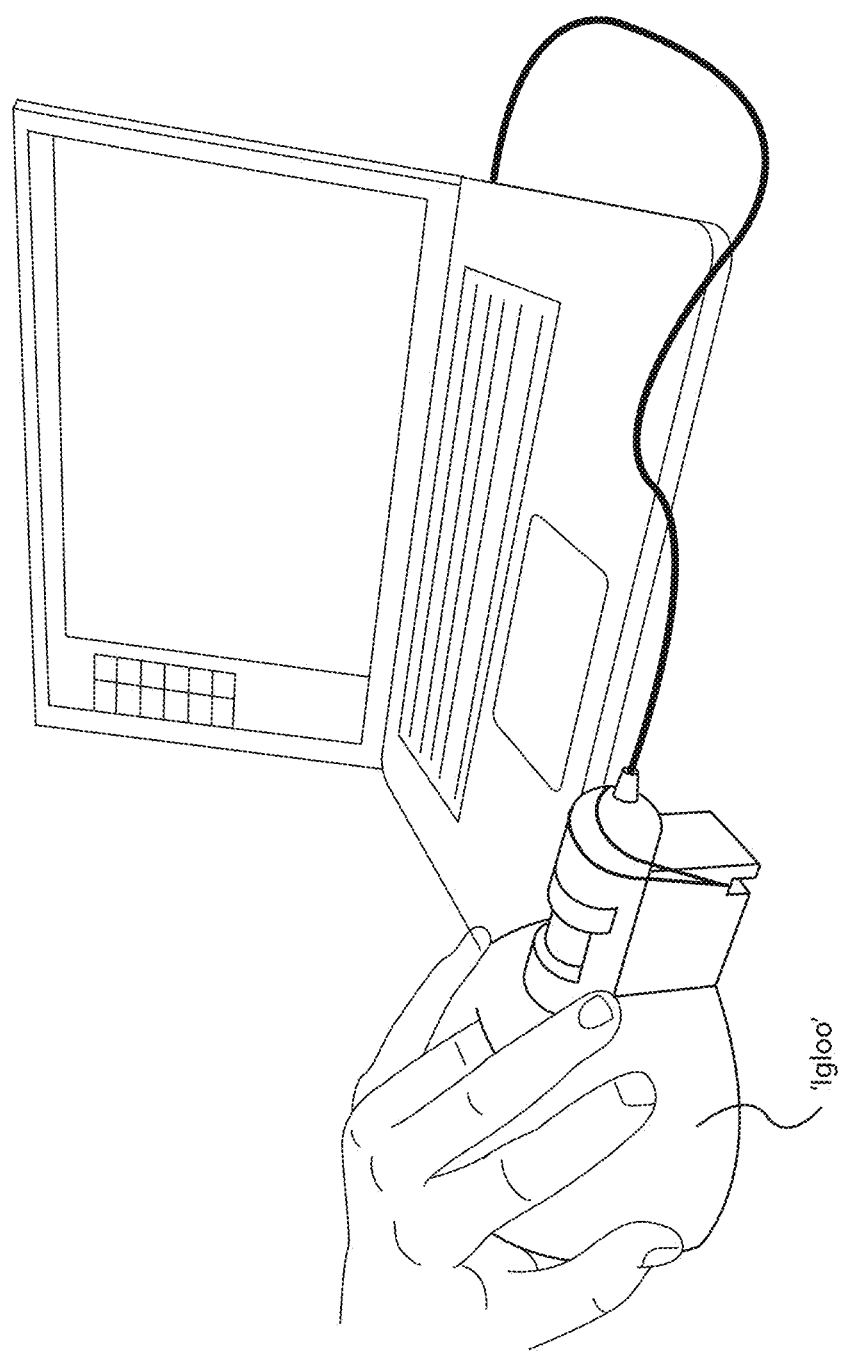

FIGS. 14A-14D are images of systems and apparatus for in vivo and non-invasive analysis of blood cell dynamics according to some embodiments. FIG. 14A shows a finger holder coupled to an imager. The imager may use a commercially available capillaroscope (e.g., Dino-Lite Digital Microscope (available from BigC.com (Torrance, Calif.)). The imager may include its own illumination source such that when a finger is placed in the finger hole, the finger is well illuminated for imaging. FIG. 14B shows an imager and a finger holder de-coupled. FIG. 14C shows a finger holder when a finger is placed in the finger hole. FIG. 14D shows a system including a finger holder, an imager, and a computer that is connected to the imager via, e.g., a USB connection. The computer may display, in real time, images or video captured by the imager. Methods described in earlier sections of this application may be saved as processor executable instructions in a memory of the computer, a processor of which then may perform analysis of the images to detect WBC events.

FIGS. 15A-15G are views of an adapter that can be attached to a smartphone for capturing images of a nail fold with a camera-equipped device for blood cell dynamics analysis in accordance with some embodiments. FIG. 15A is a perspective view of adapter 1500 including window section 1510 and a plurality of suction cups 1520. Window section 1510 may be aligned with the camera typically available in smartphones. Suction cups 1520 may secure adapter 1500 to, for example, a smartphone. While four suctions cups are shown in FIG. 15A, the number of the suction cups can be any number that is applicable. Alternatively or in addition, an adapter may be attached or secured to a smartphone or other device using a clip, adhesive, etc.

FIG. 15B shows adapter 1500 from perspective angle to illustrate the structure of window section 1510, which further includes window 1512 and finger receptor 1514. Window 1512 is substantially transparent or at least transparent at certain wavelengths so as to allow the camera to take images of fingers. Finger receptor 1514 has an internal contour that fits the general shape of fingers so as to firmly secure fingers with adapter 1500, thereby reducing burden of image registration (e.g., due to movement) in subsequent processing.

FIG. 15C is a top view of adapter 1500, FIG. 15D is a first side view of adapter 1500, and FIG. 15F is a second side view of adapter 1500. FIG. 15E is a back view of adapter 1500 illustrating illumination channel 1516 and window 1512. FIG. 15G is a front view (the side receiving the finger) of adapter 1500. As shown in FIGS. 15E and 15G, illumination channel 1516 is generally not through the entire depth of adapter 1500. Instead, illumination channel 1516 may be in optical communication with a flash light that is generally available in smartphones and other camera-equipped devices beside the camera lens. Illumination channel 1516 may receive light emitted by the flash light and reflect it toward window 1512 so as to illuminate at least a portion of the finger to be imaged.

Figure 15I:
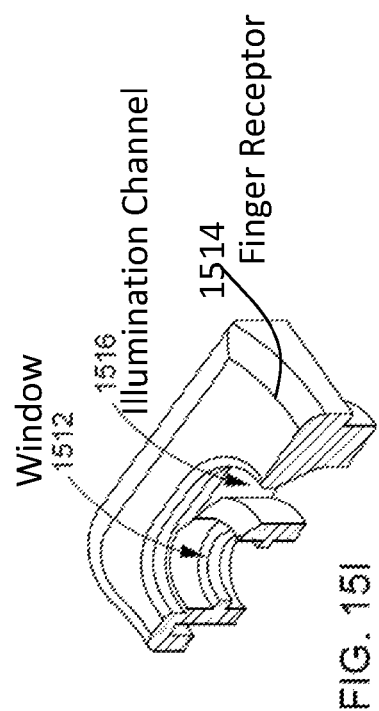
Figure 15H:
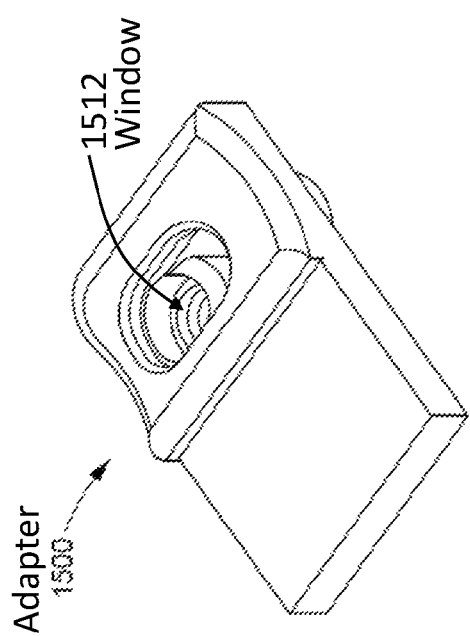
Figure 15J:
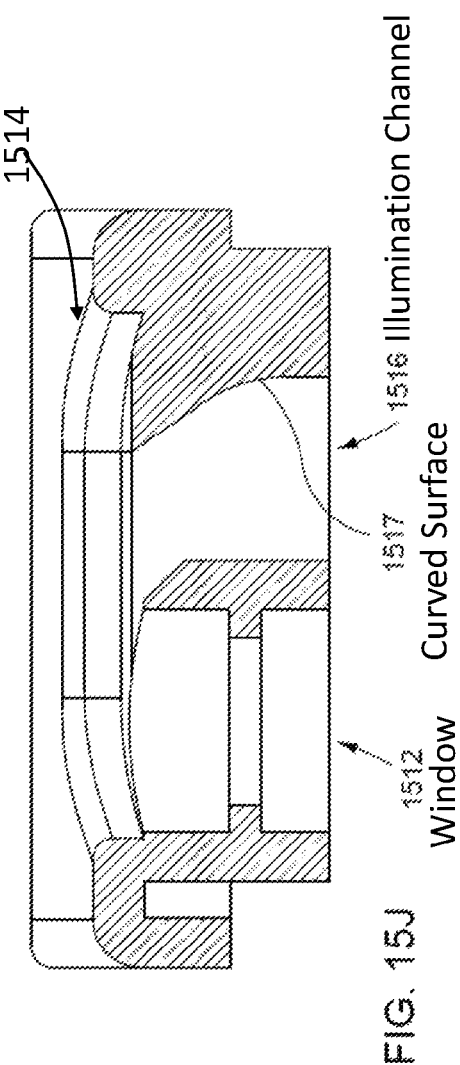

FIGS. 15H-15J illustrate illumination channel 1516. FIG. 15H is a perspective view of adapter 1500. FIG. 15I is a perspective cross-sectional view of part of adapter 1500 to illustrate window 1512 and illumination channel 1516. FIG. 15J is a cross-sectional view of adapter 1500 to illustrate structures of illumination channel 1516. In particular, illumination channel 1516 may include a curved surface 1517 that reflects received light toward window 1512 so as to illuminate a finger typically disposed in front of window 1512 for imaging.

FIG. 16 is a schematic of a system including a smartphone and an adapter for capturing images of a nail fold for blood cell dynamics analysis in accordance with some embodiments. Adapter 1600 includes window 1612 in optical communication with camera 1632 of smartphone 1630. Adapter 1600 also includes illumination channel 1616 in optical communication with LED light 1636 of smartphone 1630. Illumination channel 1616 receives light emitted by LED light 1636, and curved surface 1617 in illumination channel 1616 reflects the received light toward window 1612 so as to illuminate the finger 1640 (more specifically nailfold 1642), which is in close contact with window 1612.

In some embodiments, window 1612 may include two lenses to change the focal length of camera 1632 in smartphone 1630. Changing the focal length can also change the resolution of the images taken by camera 1632. In some examples, index matched fluid 1618 may be disposed between window 1612 and nailfold 1642. Index matched fluid 1618 may have a refractive index similar to that of a nailfold or of the material of window 1612 so as to reduce specular reflection at the surface of window 1612 or at the surface of nailfold 1642. In some embodiments, index matched fluid 1618 has high viscosity. In some embodiments, index matched fluid 1618 may be replaced by a compliant reusable transparent plastic.

Figure 17B:
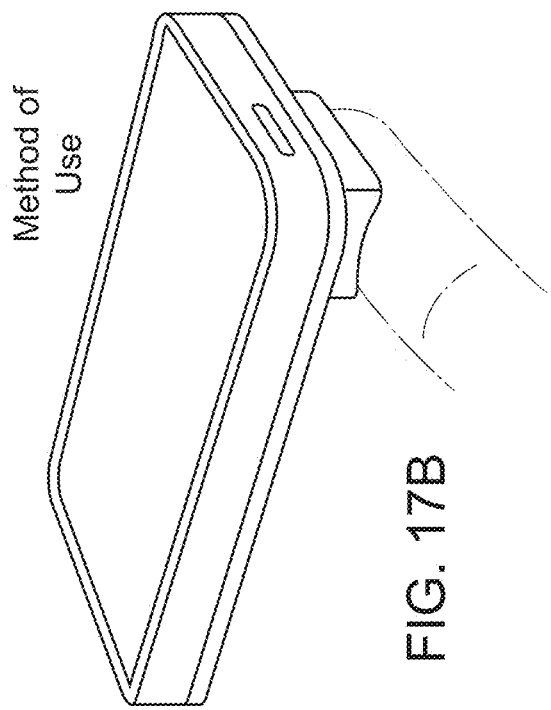
FIGS. 17A-17B are images of a system including a smartphone and an adapter for capturing images of a nailfold for blood cell dynamics analysis in accordance with some embodiments.
Figure 17A:
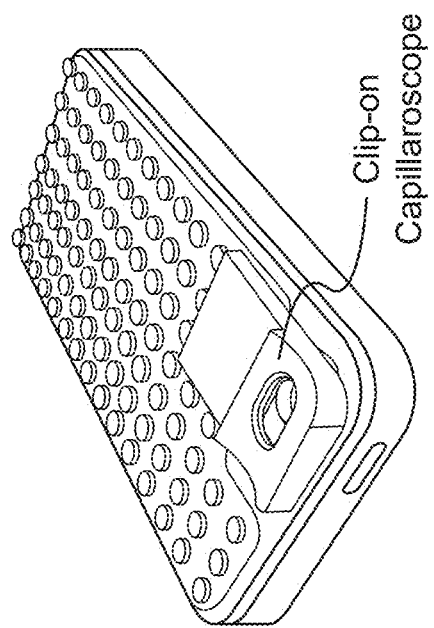
Figure 18:
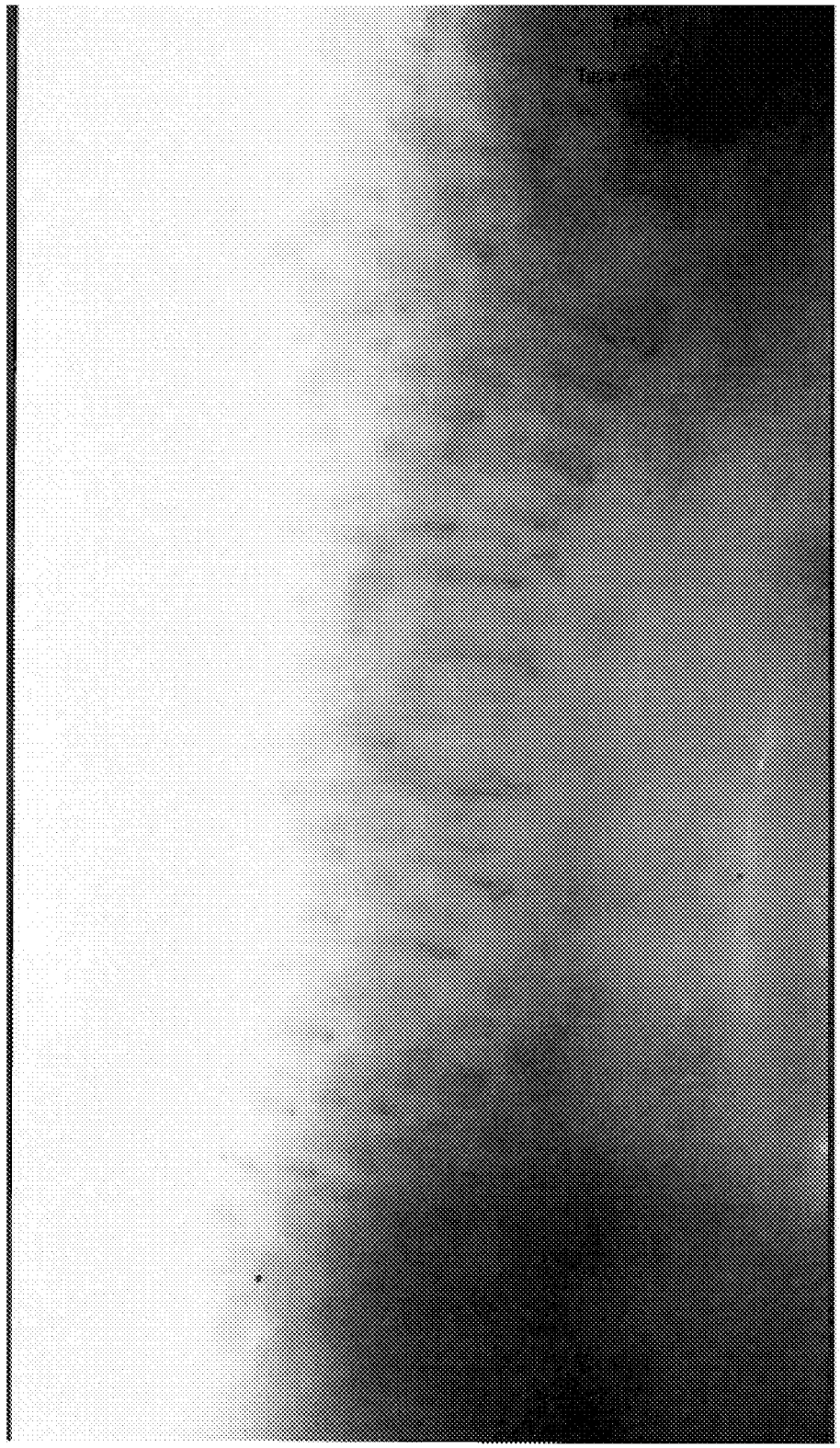
FIG. 18 is an example image captured by the system shown in FIGS. 17A-17B in accordance with some embodiments.

FIG. 17A shows a smartphone with an adapter attached to the smartphone so as to allow image taking of a nailfold according to some embodiments. FIG. 17B shows the smartphone and the adapter when a finger is placed in front of the adapter for imaging. FIG. 18 is an image captured by the smartphone using the adapter shown in FIGS. 17A-17B. Multiple capillary structures are visible in the image for further analysis of blood cell dynamics in accordance with some embodiments.

Figure 19:
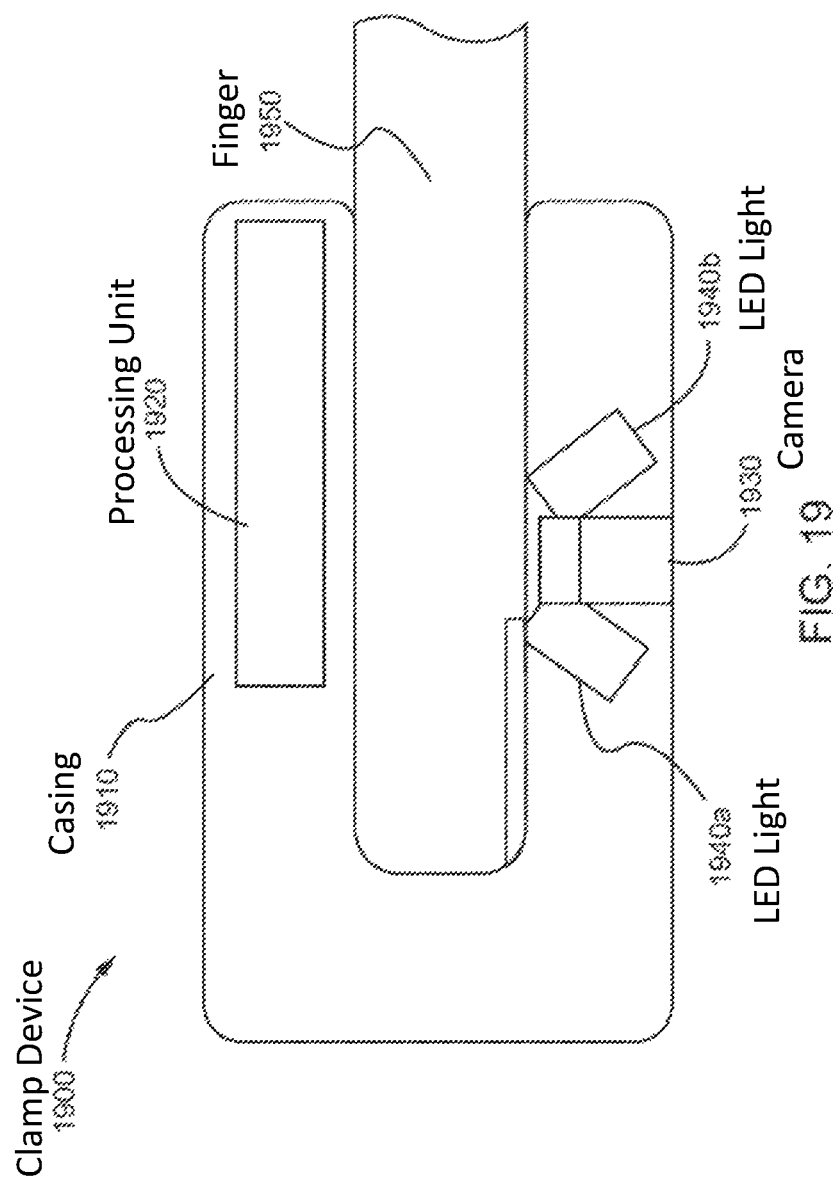
FIG. 19 is a schematic of a clamp device for performing blood cell dynamics analysis from images of a nailfold in accordance with some embodiments.
Figure 20:
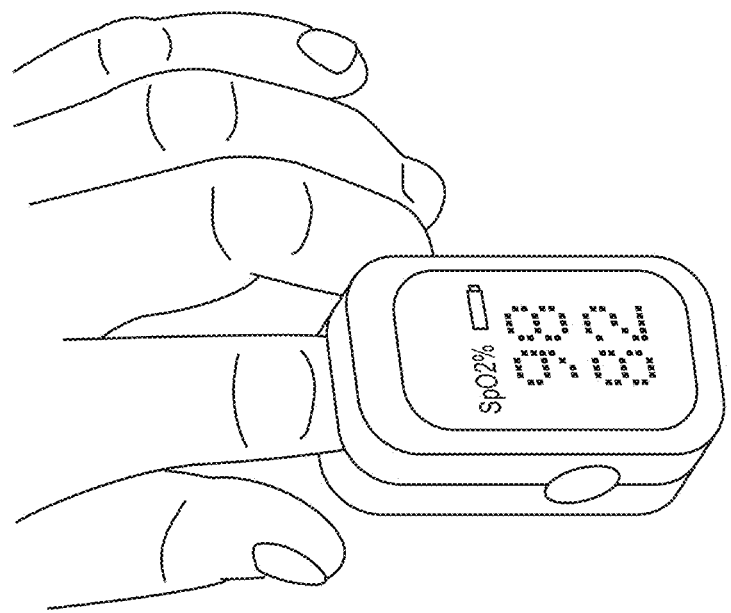
FIG. 20 is an image of a clamp device being used to capture images of a nailfold and analyzing blood cell dynamics.

FIG. 19 is a schematic of a clamp device for capturing images and performing blood cell dynamics analysis according to some embodiments. Clamp device 1900 includes spring-loaded casing 1910 for securely receiving finger 1950. When finger 1950 is placed in clamp device 1900, camera 1930 can take images of finger 1950 with finger 1950 illuminated by a pair of LED lights 1940a and 1940b. In some embodiments, LED lights 1940a and 1940b emit broad-spectrum white light. In some embodiments, LED lights 1940a and 1940b emit green light which can be effectively reflected by WBCs. Clamp device also may include a battery and/or processing unit 1920 for processing images taken by camera 1930 according to methods described above. FIG. 20 shows a clamp device coupled with a finger for blood cell dynamics analysis. As can be seen from FIG. 20, the spring-loaded casing helps to secure the finger with the clamp device so as to reduce or eliminate relative movement between the finger and the camera.

Figure 21A:
FIGS. 21A-21F and 21G-21O are images and wireframes, respectively, of a smartphone adapter for capturing images of a nailfold with a smartphone camera for capillaroscopy and hematology analysis in accordance with some embodiments.
Figure 21B:
Figure 21C:
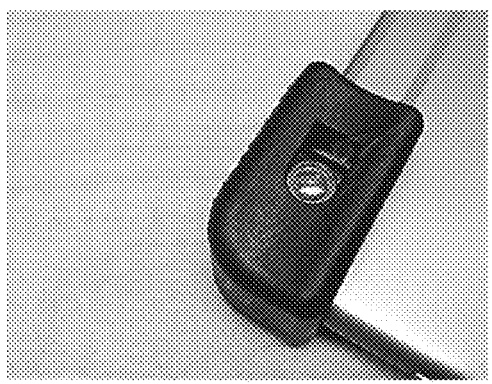
Figure 21D:
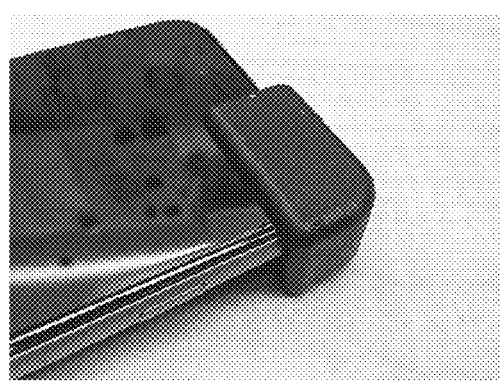
Figure 21E:
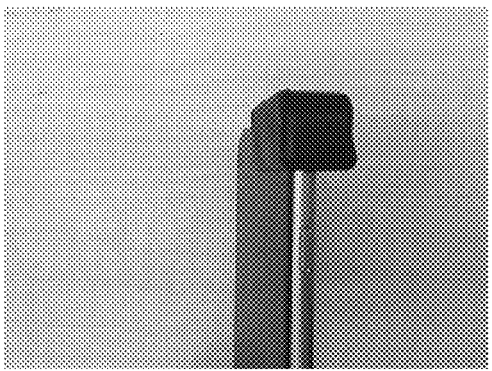
Figure 21F:
Figure 21H:
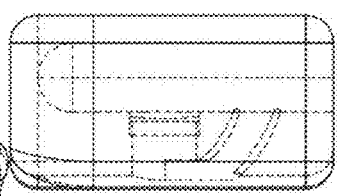
Figure 21O:
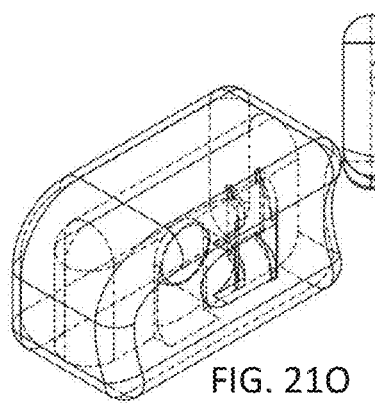
Figure 21I:
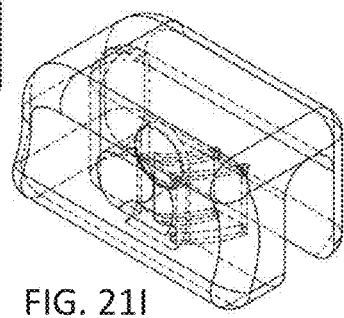
Figure 21N:
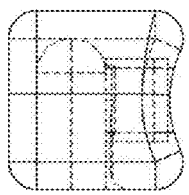
Figure 21G:
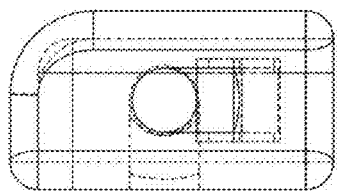
Figure 21J:
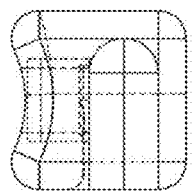
Figure 21M:
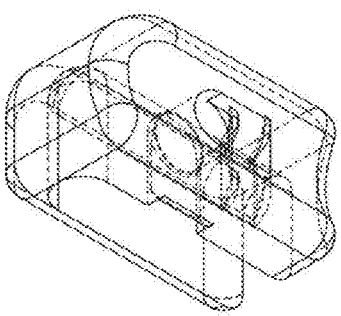
Figure 21L:
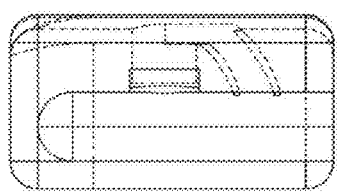
Figure 21K:
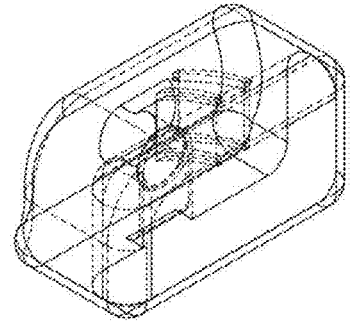
Figure 22A:
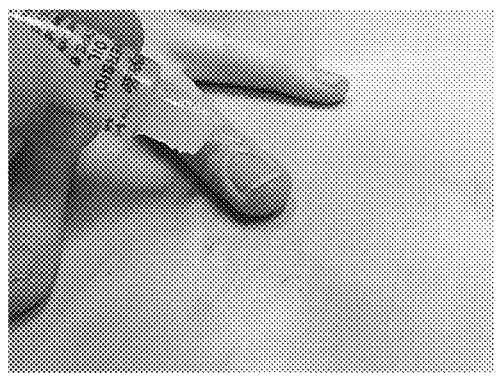
FIGS. 22A-22D are images illustrating a method of using a smartphone adapter for capturing images of a nailfold with a smartphone camera for capillaroscopy and hematology analysis in accordance with some embodiments.
Figure 22B:
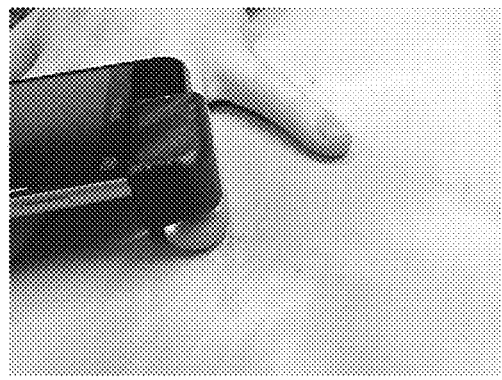
Figure 22C:
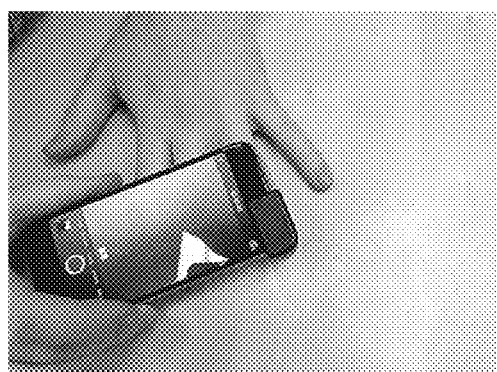
Figure 22D:
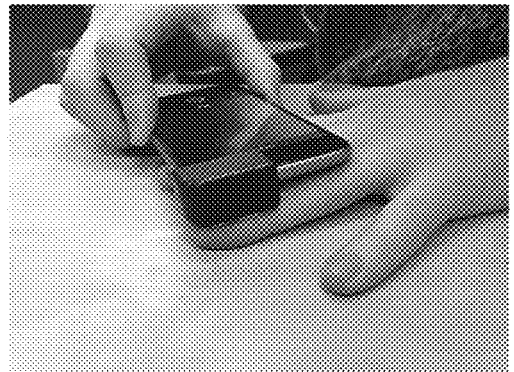

FIGS. 21A-21O are views of an adapter for capturing images of a nailfold with a smartphone camera for capillaroscopy and hematology analysis in accordance with some embodiments. In particular, FIGS. 21A-21F are images of perspective views of a smartphone adapter. In FIGS. 21A-21E, the adapter is attached to a smartphone such that the smartphone camera may be utilized. In FIG. 21F, the adapter is shown unattached. FIGS. 21G-21O are wireframes showing the side and perspective views of the adapter. FIGS. 22A-22D illustrate a method of using a smartphone adapter attached to a smartphone such that the smartphone camera may be used for capillaroscopy and hematology analysis according to some embodiments. In FIG. 22A, index matched fluid is disposed on the surface of a nail fold of a user. In FIGS. 22B-22D, the smartphone is positioned over the finger such that the adapter rests on the finger and the smartphone camera is aligned with the nailfold.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method for detecting a white blood cell (WBC) event from in vivo capillary data associated with a subject, the method comprising:
   non-invasively obtaining the capillary data, the capillary data comprising a plurality of images captured over a first time period;
   specifying a first set of two-dimensional (2D) coordinates associated with the plurality of images, the first set of 2D coordinates corresponding to a plurality of internal contour points of a capillary visible in the plurality of images;
   specifying a second set of 2D coordinates associated with the plurality of images, the second set of 2D coordinates corresponding to a plurality of external contour points of the capillary;
   interpolating the first set of 2D coordinates to generate a first set of resampled coordinates;
   interpolating the second set of 2D coordinates to generate a second set of resampled coordinates;
   generating a plurality of intermediate curves based on the first set of resampled coordinates and the second set of resampled coordinates, the plurality of intermediate curves including a middle curve;
   defining a plurality of curvilinear distances based on the middle curve;
   extracting a plurality of intensity values from the plurality of images, each extracted intensity value corresponding to one of the plurality of images, one of the plurality of intermediate curves, and one of the plurality of curvilinear distances;
   transforming the plurality of extracted intensity values to a Radon domain;
   identifying a plurality of maxima locations corresponding to a flow trajectory inside the capillary; and
   detecting at least one visual gap in the flow trajectory inside the capillary, the at least one visual gap indicating the WBC event.

2. The method of claim 1, wherein the plurality of images are obtained from nailfold capillaroscopy video.

3. The method of claim 1, wherein the plurality of images are obtained from video with a frame rate of 10 frames per second to 25 frames per second.

4. The method of claim 1, wherein the plurality of images are obtained from video with a camera pixel size of 0.5 μm to 5 μm.

5. The method of claim 1, wherein the plurality of images are a three-dimensional image stack, the stack comprising:
   a horizontal frame size of 640 pixels to 2560 pixels;
   a vertical frame size of 480 pixels to 1280 pixels; and
   a plurality of frames from 50 frames to 1000 frames.

6. The method of claim 1, wherein the plurality of images are single-channel images.

7. The method of claim 1, wherein:
   the plurality of images includes at least one multi-channel image; and
   obtaining the capillary data comprises converting the at least one multi-channel image to a single-channel image.

8. The method of claim 7, wherein converting the at least one multi-channel image to the single-channel image comprises:

averaging each channel pointwise to generate a plurality of average intensity values corresponding to each two-dimensional location in the at least one multi-channel image; and
normalizing the plurality of average intensity values to obtain the single-channel image.

9. The method of claim 1, wherein obtaining the capillary data comprises registering each image in the plurality of images to compensate for camera movement.

10. The method of claim 1, wherein:
the first set of 2D coordinates includes $N_p$ coordinates and the second set of 2D coordinates includes $N_p$ coordinates,
wherein the method further comprises:
interpolating the first set of 2D coordinates and the second set of 2D coordinates using cubic-spline interpolation with a resampling factor $\alpha$ to generate:
the first set of resampled coordinates such that the first set of resampled coordinates includes $\alpha(N_p-1)+1$ coordinates; and
the second set of resampled coordinates such that the second set of resampled coordinates includes $\alpha(N_p-1)+1$ coordinates;
wherein $N_p$ is 3 to 20, wherein $\alpha$ is 20 to 300.

11. The method of claim 1, further comprising:
before transforming the plurality of extracted intensity values to the Radon domain, performing at least one of normalization and filtering to the plurality of extracted intensity values so as to achieve at least one of an increased contrast and decreased noise.

12. The method of claim 1, further comprising:
estimating a number of WBC events occurred during the first period of time.

13. The method of claim 1, further comprising:
estimating a speed associated with a WBC event from a plurality of images.

14. The method of claim 1, further comprising at least one of diagnosing and monitoring a condition of the subject based on at least one of a number of WBC events during the firstperiod of time and a speed associated with a WBC event.

15. The method of claim 14, wherein the condition of the subject comprises at least one of a bacterial infection, a viral infection, a bone marrow functionality, and a haematologicproliferative process.

16. An apparatus for detecting a white blood cell (WBC) event from in vivo capillary data associated with a subject, the apparatus comprising:
an imager to take the capillary data, the capillary data comprising a plurality of images captured over a first time period;
a memory to store processor executable instructions; and
a processor coupled to the imager and the memory, wherein upon execution of the processor executable instruction by the processor, the processor:
receives the plurality of images captured by the imager;
receives a first set of two-dimensional (2D) coordinates associated with the plurality of images, the first set of 2D coordinates corresponding to a plurality of internal contour points of a capillary visible in the plurality of images;
receives a second set of 2D coordinates associated with the plurality of images, the second set of 2D coordinates corresponding to a plurality of external contour points of the capillary;
interpolates the first set of 2D coordinates to generate a first set of resampled coordinates;
interpolates the second set of 2D coordinates to generate a second set of resampled coordinates;
generates a plurality of intermediate curves based on the first set of resampled coordinates and the second set of resampled coordinates, the plurality of intermediate curves including a middle curve;
defines a plurality of curvilinear distances based on the middle curve;
extracts a plurality of intensity values from the plurality of images, each extracted intensity value corresponding to one of the plurality of images, one of the plurality of intermediate curves, and one of the plurality of curvilinear distances;
transforms the plurality of extracted intensity values to a Radon domain;
identifies a plurality of maxima locations corresponding to a flow trajectory inside the capillary; and
detects at least one visual gap in the flow trajectory inside the capillary, the at least one visual gap indicating the WBC event.

17. The apparatus of claim 16, further comprising:
a display device, wherein upon execution of the processor executable instruction by the processor, the processor controls the display device to display a representation of theWBC event.

18. The apparatus of claim 17, wherein upon execution of the processor executable instruction by the processor, the processor controls the display device to display the pluralityof images.

19. The apparatus of claim 16, further comprising:
a subject holder to receive at least a portion of a human finger so as to facilitate the imager to take the plurality of images.

20. The apparatus of claim 16, further comprising a smartphone, wherein the smartphone comprises the imager, the memory, and the processor.

21. The apparatus of claim 16, wherein imager comprises a nailfold capillaroscope and the plurality of images are obtained from nailfold capillaroscopy video.

22. The apparatus of claim 16, wherein the imager is configured to take the plurality of images with a frame rate of 10 frames per second to 25 frames per second.

23. The apparatus of claim 16, wherein the imager has pixel size of 0.5 μm to 5 μm.

24. The apparatus of claim 16, wherein the plurality of images are a three-dimensional image stack, the stack comprising:
a horizontal frame size of 640 pixels to 2560 pixels;
a vertical frame size of 480 pixels to 1280 pixels; and
a plurality of frames from 50 frames to 1000 frames.

25. The apparatus of claim 16, wherein the plurality of images are single-channel images.

26. The apparatus of claim 16, wherein the plurality of images includes at least one multi-channel image, wherein upon execution of the processor executable instruction by the processor, the processor converts the at least one multi-channel image to a single-channel image.

27. The apparatus of claim 26, wherein upon execution of the processor executable instruction by the processor, the processor:
averages each channel pointwise to generate a plurality of average intensity values corresponding to each two-dimensional location in the at least one multi-channel image; and
normalizes the plurality of average intensity values to obtain the single-channel image.

28. The apparatus of claim 16, wherein upon execution of the processor executable instruction by the processor, the processor registers each image in the plurality of images to compensate for camera movement.

29. The apparatus of claim 16, wherein:
the first set of 2D coordinates includes $N_p$ coordinates and the second set of 2D coordinates includes $N_p$ coordinates,
wherein upon execution of the processor executable instruction by the processor, the processor further:
interpolates the first set of 2D coordinates and the second set of 2D coordinates using cubic-spline interpolation with a resampling factor α to generate:
the first set of resampled coordinates such that the first set of resampled coordinates includes $\alpha(N_p-1)+1$ coordinates; and
the second set of resampled coordinates such that the second set of resampled coordinates includes $\alpha(N_p-1)+1$ coordinates;
wherein $N_p$ is 3 to 20, wherein α is 20 to 300.

30. The apparatus of claim 16, wherein upon execution of the processor executable instruction by the processor, the processor:
before transforming the plurality of extracted intensity values to the Radon domain, performs at least one of normalization and filtering to the plurality of extracted intensity values so as to achieve at least one of an increased contrast and decreased noise.

31. The apparatus of claim 16, wherein upon execution of the processor executable instruction by the processor, the processor further:
estimates a number of WBC events occurred during the first period of time.

32. The apparatus of claim 16, wherein upon execution of the processor executable instruction by the processor, the processor further:
estimates a speed associated with a WBC event from a plurality of images.

33. A non-transitory computer-readable medium encoded with instructions that, when executed on at least one processing unit, perform a method for detecting a white blood cell (WBC) event from in vivo capillary data associated with a subject, the method comprising:
non-invasively obtaining the capillary data, the capillary data comprising a plurality of images captured over a first time period;
specifying a first set of two-dimensional (2D) coordinates associated with the plurality of images, the first set of 2D coordinates corresponding to a plurality of internal contour points of a capillary visible in the plurality of images;
specifying a second set of 2D coordinates associated with the plurality of images, the second set of 2D coordinates corresponding to a plurality of external contour points of the capillary;
interpolating the first set of 2D coordinates to generate a first set of resampled coordinates;
interpolating the second set of 2D coordinates to generate a second set of resampled coordinates;
generating a plurality of intermediate curves based on the first set of resampled coordinates and the second set of resampled coordinates, the plurality of intermediate curves including a middle curve;
defining a plurality of curvilinear distances based on the middle curve;
extracting a plurality of intensity values from the plurality of images, each extracted intensity value corresponding to one of the plurality of images, one of the plurality of intermediate curves, and one of the plurality of curvilinear distances;
transforming the plurality of extracted intensity values to a Radon domain;
identifying a plurality of maxima locations corresponding to a flow trajectory inside the capillary; and
detecting at least one visual gap in the flow trajectory inside the capillary, the at least one visual gap indicating the WBC event.

\* \* \* \* \*

UNITED STATES PATENT AND TRADEMARK OFFICE
CERTIFICATE OF CORRECTION

PATENT NO. : 9,984,277 B2
APPLICATION NO. : 14/951260
DATED : May 29, 2018
INVENTOR(S) : Castro-Gonzalez et al.

Page 1 of 1

It is certified that error appears in the above-identified patent and that said Letters Patent is hereby corrected as shown below:

In the Claims

- Column 23, In Claim 14, Line 4, replace "firstperiod" with --first period--.
- Column 23, In Claim 15, Lines 3-4, replace "haematologicproliferative" with --haematologic proliferative--.
- Column 24, In Claim 17, Line 5, replace "theWBC" with --the WBC--.
- Column 24, In Claim 18, Lines 3-4, replace "pluralityof" with --plurality of--.

Signed and Sealed this
Twelfth Day of March, 2019

Andrei Iancu
*Director of the United States Patent and Trademark Office*